US006667051B1

(12) United States Patent
Gregory

(10) Patent No.: US 6,667,051 B1
(45) Date of Patent: Dec. 23, 2003

(54) METHODS FOR PRODUCING ELASTIN, AND TROPOELASTIN PRODUCTS FOR REPAIRING AND OR REPLACING TISSUE

(75) Inventor: Kenton W. Gregory, 3737 SW. Council Crest Dr., Portland, OR (US) 97201

(73) Assignees: Kenton W. Gregory, Portland, OR (US); Providence Health System-Oregon, Seattle, WA (US)

(*) Notice: Subject to any disclaimer, the term of this patent is extended or adjusted under 35 U.S.C. 154(b) by 0 days.

(21) Appl. No.: 09/979,868

(22) PCT Filed: May 25, 2000

(86) PCT No.: PCT/US00/14621
§ 371 (c)(1),
(2), (4) Date: Nov. 28, 2001

(87) PCT Pub. No.: WO00/73399
PCT Pub. Date: Dec. 7, 2000

Related U.S. Application Data

(60) Provisional application No. 60/136,573, filed on May 28, 1999.

(51) Int. Cl.⁷ .............................................. C09J 101/00
(52) U.S. Cl. .................... 424/443; 156/331.2; 264/345; 530/353; 128/898; 606/8
(58) Field of Search ...................... 156/331.2, 94 FOR; 526/248; 523/118; 530/353; 428/63, 478.2; 424/443; 264/345; 606/8; 128/898

(56) References Cited

U.S. PATENT DOCUMENTS

| | | | |
|---|---|---|---|
| 3,559,652 A | * 2/1971 | Banitt et al. ................ 526/298 |
| 4,132,746 A | 1/1979 | Urry et al. | |
| 4,187,852 A | 2/1980 | Urry et al. | |
| 4,500,700 A | 2/1985 | Urry | |
| 4,589,882 A | 5/1986 | Urry | |
| 4,693,718 A | 9/1987 | Urry et al. | |
| 4,783,523 A | 11/1988 | Urry et al. | |
| 4,870,055 A | 9/1989 | Urry et al. | |
| 4,980,237 A | * 12/1990 | Avramova et al. ....... 428/478.2 |
| 5,064,430 A | 11/1991 | Urry | |
| 5,124,155 A | * 6/1992 | Reich .......................... 424/443 |
| 5,223,420 A | * 6/1993 | Rabaud et al. ............. 530/353 |
| 5,336,256 A | 8/1994 | Urry | |
| 5,416,074 A | * 5/1995 | Rabaud et al. ............. 530/353 |
| 5,989,244 A | 11/1999 | Gregory | |
| 5,990,379 A | 11/1999 | Gregory | |
| 6,087,552 A | 7/2000 | Gregory | |
| 6,110,212 A | 8/2000 | Gregory | |
| 6,372,228 B1 | 4/2002 | Gregory | |

OTHER PUBLICATIONS

Debra Bedell–Hogan, Philip Trackman, William Abrams, Joel Rosenbloom, Herbert Kagan. "Oxidation, Cross–Linking, and Insolubilization of Recombinant Tropoelastin by Purified Lysyl Oxidase", (Journal of Biological Chemistry, vol. 268, No. 14, pp. 10345–10350 (1993).

Ooayama et al, "Substratum–Bound Elastin Peptide Inhibits Aortic Smooth Muscle Cell Migration in Vietro" Arteriosclerosis 7(6):593–598 (1987).

Long, et al, "Elastin Repeat Peptides as Chemo attractants for Bovine Aortic Endothelial cells", Journal of Cellular Physiology 140:512–518 (1989).

Abrahamian et al. A new reconstituted connective tissue matrix: Preparation, biochemical, structural and mechanical studies:, Journal of Biomedical Materials Research 21:965–977 (1987).

Martin et al, "Biochemical study of adduct synthesis between fibrin monomers and elastin" Biomaterials 9:519–524 (1988).

Rebaud et al, "Soluble Fibrinogen Derivatives Generated by Thrombin: Affinity for Elastin", Thrombosis Research 43:205–211 (1986).

Pool, et al, "Production of High–Potency Concentrations of Antihemophilic Globulin in a Closed–Bag System", The New England Journal of Medicine 273(27):1443–1447 (1965).

Rebaud et al, "A New Biodegradable Elastin–Fibrin Material; Its use In Urological, Digestive and Cardiovascular Surgery, Journal of Biomaterials Applications", vol. 7, Jul. 1992.

* cited by examiner

*Primary Examiner*—Jeff H. Aftergut
(74) *Attorney, Agent, or Firm*—Marger Johnson & McCollom, P.C.

(57) ABSTRACT

The invention is directed to a method including the steps of providing at least one layer of unlaminated elastin or unlaminated elastin-based materials or unlaminated tropoelastin materials. Then, the unlaminated elastin or unlaminated elastin-based materials or unlaminated tropoelastin materials is subjected to heating and pressing steps. The pressing step of the present invention is preferably conducted in the presence of steam. The laminated elastin or laminated elastin-based materials or laminated tropoelastin materials preferably comprises a multi-layer composite material. Typically, the step of adhering with an adhesive material the laminated elastin or laminated elastin-based materials or laminated tropoelastin materials is employed in order to achieve a water-tight engagement with the tissue substrate. A biogradable cyanacrylate glue is generally used in order to achieve quick and easy way to secure the patch in place and provide watertight fusion instantly. Preferably, the adhesive material comprises an alkoxy alkyl cyanoacrylate material.

27 Claims, 23 Drawing Sheets

(15 of 23 Drawing Sheet(s) Filed in Color)

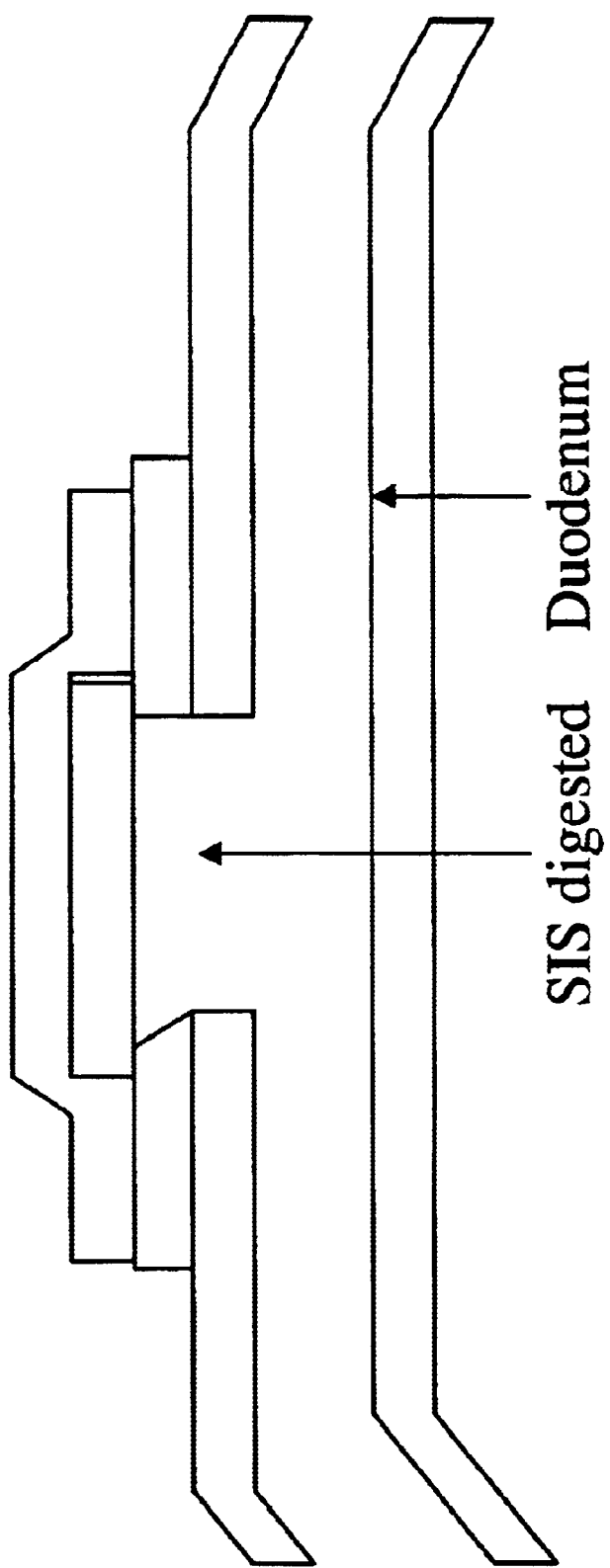

METHODS FOR PRODUCING ELASTIN, AND TROPOELASTIN PRODUCTS FOR REPAIRING AND OR REPLACING TISSUE

RELATED APPLICATIONS

This application claims benefit to provisional application No. 60/136,573 filed May 28, 1999. This application is a 371 national stage application of PCT/US00/14621 filed May 25, 2000.

This invention was made with Government support under Grant No. DAMD17-96-1-6006 awarded by U.S. Army Medical Research Acquisition Activity. The U.S. Government has certain rights in the invention.

TECHNICAL FIELD

The present invention relates to laminated elastin, laminated elastin-based biomaterials, and to laminated tropoelastin materials, to methods of producing such laminated materials, and more particularly to methods of using these laminated materials in tissue repair and replacement.

BACKGROUND OF THE INVENTION

Elastin fibers are responsible for the elastic properties of several tissues such as skin and lung, as well as arteries, and are composed of two morphologically distinct components, elastin and microfibrils. Microfibrils make up the quantitatively smaller component of the fibers and play an important role in elastic fiber structure and assembly.

The most abundant component of elastic fibers is elastin. The entropy of relaxation of elastin is responsible for the rubber-like elasticity of elastic fibers. Elastin is an extracellular matrix protein that is ubiquitous in mammals. Elastin is found, for example, in skin, blood vessels, and tissues of the lung where it imparts strength, elasticity and flexibility. In addition, elastin, which is prevalent in the internal elastic lamina (IEL) and external elastic lamina (EEL) of the normal artery, may inhibit the migration of smooth muscle cells into the intima. Elastin in the form of solubilized peptides has been shown to inhibit the migration of smooth muscle cells in response to platelet-derived factors (Ooyambia et al, Arter iosclerosis 7:593 (1987). Elastin repeat hexapeptides attract bovine aortic endothelial cells (Long et al, J. Cell. Physiol. 140:512 (1989) and elastin nonapeptide s have been shown to attract fibroblasts (U.S. Pat. No. 4,976,734). The present invention takes advantage of these physical and biochemical properties of elastin.

Thirty to forty percent of atherosclerotic stenoses are opened with balloon angioplasty restenose as a result of ingrowth of medial cells. Smooth muscle ingrowth into the intima appears to be more prevalent in sections of the artery where the IEL of the artery is ripped, torn, or missing, as in severe dilatation injury from balloon angioplasty, vessel anastomoses, or other vessel trauma that results in tearing or removal of the elastic lamina. While repair of the arterial wall occurs following injury, the elastin structures IEL and EEL do not reorganize. Since these components play major structural and regulatory roles, their destruction is accompanied by muscle cell migration. There are also diseases that are associated with weakness in the vessel wall that result in aneurysms that can ultimately rupture, as well as other events that are, at least in part, related to abnormalities of elastin.

In vertebrates elastin is formed through the secretion and crosslinking of tropoelastin, the 72-kDa biosynthetic precursor to elastin. This is discussed, for example, in an article entitled "Oxidation, Cross linking, and Insolubilization of Recombinant Crosslinked Tropoelastin by Purified Lysyl Oxidase" by Bedell Hogan, et al in the Journal of Biological Chemistry, Vol. 268, No. 14, on pages 10345 10350 (1993).

In vascular replacement and repair, the best current option is to implant autologous veins and arteries where the obvious limit is the supply of vessels which can be sacrificed from the tissues they were intended to service. Autologous vein replacements for damaged arteries also tend to be only a temporary measure since they can deteriorate in a few years in high pressure arterial circulation.

When autologous graft material is not available, a surgeon must choose between sacrificing the vessel, and potentially the tissue it sub-served, or replacing the vessel with synthetic materials such as Dacron or Gore tex. Intravascular compatibility indicate that several "biocompatible polymers", including Dacron, invoke hyperplastic response, with inflammation particularly at the interface between native tissue and the synthetic implant. Incomplete healing is also due, in part, to a compliance mismatch between currently used synthetic biomaterials and native tissues.

As described in the prior co-pending patent applications assigned to the assignees of this application set forth above (patent application Ser. No. 08/798,426 filed Feb. 7, 1997, Ser. No. 08/797,770 filed Nov. 19, 1998, Ser. No. 08/798, 425 filed Feb. 7, 1997, Ser. No. 09/000,604 filed Dec. 30, 1997, and U.S. Pat. No. 5,989,244, issued Nov. 23, 1999, and U.S. Pat. No. 5,990,379 issued Nov. 23, 1999) all of which are incorporated herein by reference, elastin and elastin-based biomaterials, or tropoelastin materials, can be used in a number of medical applications. For example, these materials can be employed to provide a method of effecting repair or replacement or supporting a section of a body tissue, as a stent, such as a vascular stent, or as conduit replacement, or as an artery, vein or a ureter replacement, or as a stent or conduit covering or coating or lining. It can also provide a graft suitable for use in repairing a lumen wall, or in tissue replacement or repair in, for example, interior bladder replacement or repair, intestine, tube replacement or repair such as fallopian tubes, esophagus such as for esophageal varicies, ureter, artery such as for aneurysm, vein, stomach, lung, heart such as congenital cardiac repair, or colon repair or replacement, or skin repair or replacement, or as a cosmetic implantation or breast implant.

Surgical repair of major injury to the duodenum for example, with significant tissue los, requires innovative surgical techniques, and is associated with significant morbidity and mortality. Segmental resection and primary end to end anastomosis is not possible in this region due to its close proximity to the head of pancreas, and connections with common bile duct and pancreatic duct. Small defects can be repaired by primary closure, which will result in stricture of the duodenum depending on the amount of tissue loss. Large defects cannot be repaired this way. It will require innovative techniques, such as creation of a Jejunal patch, duodenojejunostomy, serosal onlay patch, pyloric exclusion with gastrojejunostomy, or even pancreatico duodenectomy. The last procedure is fairly extensive, and is not likely to be tolerated by acutely injured patients with other multiple injuries. The first three procedures can be done, but they still require long surgery time involving additional bowel anastomosis, and are feasible only when the jejunum is intact. Pyloric exclusion is accompanied by prolonged external drainage of the duodenal content, which makes it difficult to manage fluid and electrolyte balance, and high incidence of intraabdominal infection, sepsis and chronic fistula formation, predisposing the victim to prolonged intensive care, parenteral nutrition, hospitalization, and disability. This is due to the high content of electrolyte and digestive enzymes in the duodenal fluid, which comes mainly from bile and pancreatic excretion. As a result, prolonged leakage of duodenal content is associated with prolonged and extensive tissue loss and sepsis. Recent development in antibiotics and intensive care has significantly reduced the mortality rate from this condition but morbidity is still high.

SUMMARY OF THE INVENTION

The use of the subject laminated elastin and/or elastin based biomaterials and/or tropoelastin materials, typically in the form of a heterograft, which can employ a biodegradable glue or adhesive material, and which can be used for repair of defects such described above with respect to the duodenom. The elastin and/or elastin-based biomaterials and/or tropoelastin, in laminated form, can be used to provide a reliable barrier to repair or replace a tissue substrate, typically injured or diseased human tissue. The subject biodegradable glue provides quick and easy water tight tissue fusion between the laminated materials and the tissue substrate.

A technique has been developed that can easily, quickly, and reliably repair the injury to organs, such as the duodenum, without compromising the lumen. It should result in a much faster recovery with less complications, morbidity, and mortality. The laminated elastin and/or elastin based biomaterials and/or tropoelastin can be used to repair such defect without compromising the lumen. Also, in the case of the duodenum there is no need for other bowel anastomosis, or extensive resection. This laminated material was shown to be biologically inert, inducing minimal immunological response, and to be resistant to infection, and hydrochloric acid.

More specifically, a method is provided herein for producing the above-described laminated elastin or laminated elastin-based materials or laminated tropoelastin materials. The laminated elastin or laminated elastin-based materials or laminated tropoelastin materials is capable of being attached to a tissue substrate for repair or replacement thereof. The tissue substrate can comprise either a human or animal tissue.

The method comprises the steps of providing at least one layer of unlaminated elastin or unlaminated elastin-based materials or unlaminated tropoelastin materials. Then, the unlaminated elastin or unlaminated elastin-based materials or unlaminated tropoelastin materials is subjected to heating and pressing steps. The pressing step of the present invention is preferably conducted in the presence of steam. Preferably, depending on the thickness and nature of the unlaminated material and the desired laminated material final properties, the preferred pressure applied is from about 40 psi up to about 2000 psi, and the preferred temperature during pressing is from about 50 degrees C. up to about 170 degrees C.

The laminated elastin or laminated elastin-based materials or laminated tropoelastin materials preferably comprises a multi-layer composite material. More preferably, the laminated elastin or laminated elastin-based materials or laminated tropoelastin materials are bilaminar pressed materials.

Typically, the step of adhering with an adhesive material the laminated elastin or laminated elastin-based materials or laminated tropoelastin materials is employed in order to achieve a water-tight engagement with the tissue substrate. A biogradable cyanacrylate glue is generally used in order to achieve quick and easy way to secure the patch in place and provide watertight fusion instantly. Preferably, the adhesive material comprises a cyanoacrylate material. More preferably, the cyanoacrylate material comprises an alkoxy alkyl cyanoacrylate material.

The method of this invention can also include the step of suturing the laminated elastin or laminated elastin-based materials or laminated tropoelastin materials to the tissue substrate. Preferably, the suturing step is affected without substantial tearing of the laminated elastin or laminated elastin-based materials or laminated tropoelastin materials.

Further objects and advantages of the invention will be clear from the description that follows.

BRIEF DESCRIPTION OF THE DRAWINGS

The file of this patent contains at least one drawing executed in color.

FIG. 4A is a schematic representation of a laminated duodenal patch repair employing laminated elastin sandwiched by SIS being digested in the duodenum.

DETAILED DESCRIPTION OF A PREFERRED EMBODIMENT

Figure 1:
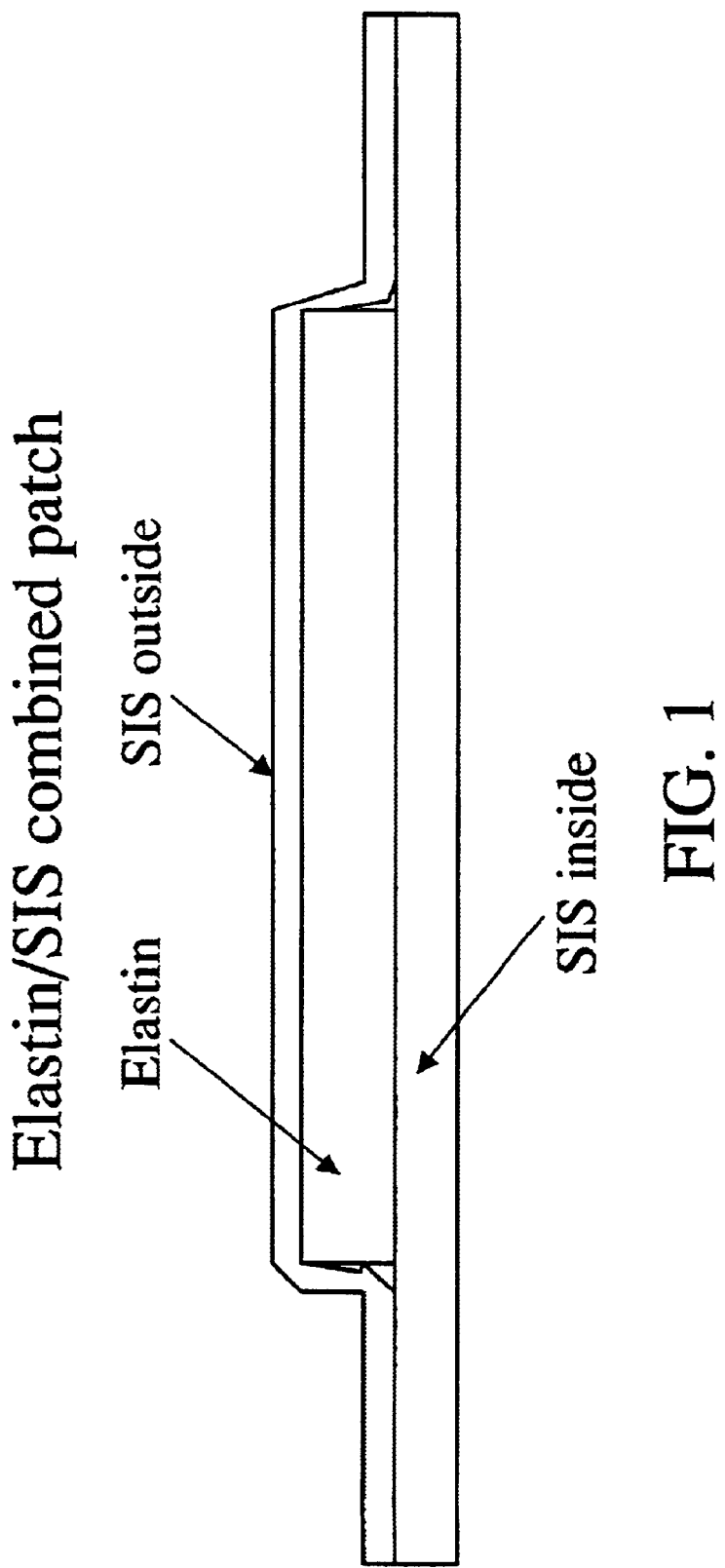
FIG. 1 is a schematic representation of a laminated Elastin/SIS composite patch of the present invention.

Elastin-based biomaterials suitable for use in the present invention can be prepared, for example, from elastin (e.g. from bovine nuchal ligament), fibrinogen and thrombin as described by Rabaud et al (U.S. Pat. No. 5,223,420). (See also Aprahamian et al, J. Biomed. Mat. Res. 21:965 (1987); Rabaud et al, Thromb. Res. 43:205 (1986); Martin, Biomaterials 9:519 (1988).) Such biomaterials can have associated thrombogenic property that can be advantageous in certain types of tissue substrate repair. Elastin-based biomaterials suitable for use in the invention can also be prepared from elastin and type III collagen, also as described by Rabaud and co-workers (Lefebvre et al, Biomaterials 13(1):28–33 (1992). Such preparations are not thrombogenic and thus can be used for vascular stents, etc. A further type of elastin-based biomaterial suitable for use in the present invention is prepared as described by Urry et al (see, for example, U.S. Pat. Nos. 4,132,746 and 4,500,700) (See also U.S. Pat. Nos. 4,187,852, 4,589,882, 4,693,718, 4,783,523, 4,870,055, 5,064,430, 5,336,256). All of these issued patents are incorporated into this application by reference. Elastin matrixes resulting from digestion of elastin-containing tissues (eg arteries) can also be used. Digestion results in the removal of cells, proteins and fats but maintenance of the intact elastin matrix. The biomaterial used will depend on the particular application.

Elastin-based biomaterial of the invention prepared from soluble elastin (see Rabaud et al above) can be molded so as to render it a suitable size and shape for any specific purpose. Molded biomaterial can be prepared as follows. Elastin (eg soluble elastin (MW 12–32,000 daltons) is washed and swollen in buffer. Fibrinogen or cryoglobulins (prepared, for example, according to Pool et al, New Engl. J. Med. 273 (1965 are added to the swollen elastin, followed by thiourea, with or without a protease inhibitor (such as aprotinin), and collagen. Thrombin is added with stirring and the resulting mixture is immediately poured into an appropriate mold. The mold is then incubated (for example, at 37 Degrees C.) while polymerization of the fibrin/elastin material is allowed to proceed, advantageously, for from between 15 minutes to 1 hour, 30 minutes being preferred. The reaction can be carried out at temperatures less than 37 Degrees C., but the reaction proceeds more rapidly at 77 Degrees C. Heating the reaction to over Degrees C., however, can result in denaturation of the thrombin. Cooling of the mixture while stirring allows more time for mixing to occur. For polymerization to occur, it is important to have calcium and magnesium in the buffer and to use undenatured thrombin.

Following polymerization in the mold, the resulting biomaterial can be further cross-linked using gamma radiation or an agent such as glutaraldehyde (a solution of glutaraldehyde, formic acid and picric acid being preferred). When radiation is used, the samples are, advantageously, subjected to gamma-irradiation from a Cobalt-60 source. The amount of irradiation can range, for example, from 10 to 100 MRAD, with 25 MRAD being preferred. It has been shown that the amount of gamma-irradiation can affect the strength of the material (Aprahamian, J.Biomed. Mat. Res. 21:965(1987).

Sheets of unlaminated biomaterial can be prepared that are of a controlled thicknesses by using appropriate molds. Sheets of this biomaterial can be made in thicknesses ranging, for example, from 200 microns to 5 mm. By way of example, a sheet suitable for use as an intestinal patch can range in thickness from 200 microns to 5 mm, with about 2 mm being preferred. A patch requiring greater strength, such a patch for use in the bladder, is typically thicker. Arterial patches can be thinner, e.g., 100 um–1000 um.

Biomaterial prepared from soluble elastic or insoluble elastin fragments can also be molded into tubular segments for example, by injecting the material into tubular molds. Crosslinkage of the elastin solution present between the inner and outer tubes can be effected prior to withdrawal of biomaterial from the mold or after the tubes are removed. Tubular segments of different inner and outer diameters, as well as of different lengths, can be prepared using this approach by varying the diameters of the inner and outer tubes. A mold of this type can be made in virtually any size with the inner and outer tubes varying in diameter. A small tube can be used for a coronary arterial stent. A large tube of 1–5 inches in diameter can be made and used as an angularly welded patch for anastomosis of the small intestine or colon. Various molding techniques and molding materials can be used; the foregoing is merely an example.

As indicated above, biomaterial suitable for use in the present invention can be prepared from digests of tissue containing an elastin matrix. Tissues suitable for use as a starting material include arteries (e.g. coronary or femoral arteries, for example, from swine), umbilical cords, intestines, ureters, etc. Preferably, the matrix material is (derived from the species of animal in which the implantation is being performed so that bio compatibility is increased. Any method of removing (digesting away) cellular material, proteins and fats from the native matrix while leaving the extracellular elastin matrix intact can be used. These methods can involve a combination of acidic, basic, detergent, enzymatic, thermal or erosive means, as well as the use of organic solvents. This may include incubation in solutions of sodium hydroxide, formic acid, trypsin, guanidine, ethanol, diethylether, acetone, t-butanol, and sonication. Typically, the digestion proceeds more quickly at higher temperatures. The optimal temperature and time (of incubation depend on the starting material and digestive agent used and can be readily determined.

The biomaterial of the invention, whether prepared from elastin powder or from tissues digests, is normally secured to existing tissue substrate. Various techniques for effecting that attachment can be used, including art-recognized techniques. For example, biomaterial can be secured using a tissue substrate welding energy source and an agent that absorbs energy emitted by that source. This technique is described in detail in the above referenced U.S. Patents and U.S. patent application which are assigned to the assignee herein. (All of which have been incorporated herein by reference.)

The laminated elastin and/or elastin biomaterial and or tropoelastin as previously described herein can be employed as a patch material ("Elastin Patch") for use in, for example, intestinal or colon repairs which frequently do not heal well with current techniques, particularly when the patient has nutritional or other problems or when the patient is in shock, such as in the case of multiple gunshot wounds or other abdominal injuries. The use of such an Elastin Patch can, for example, seal off intestinal contents and thereby reduce the likelihood of peritonitis. The use of an Elastin Patch will be described in detail below. In addition, a patch can be used on a solid organ, such as the liver, when lacerations have occurred. Similarly, the biomaterial of the invention can be used to repair or replace portions of the urinary system i.e., from the calyces of the kidney on down to the urethra. The patch can also be used to seal a defect in a cardiac chamber, such as an atrial septal defect, as well as bronchial or rectal fistulas. The laminated biomaterial can also be used as a cerebrovascular patch for an aneurysm. The laminated biomaterial can be sealed in place with targeted laser fusion. For applications where direct exposure is not possible or not desirable, a variety of catheter or endoscopic systems can be employed to direct the laser energy to the target site.

The laminated elastin, elastin-based biomaterial or tropoelastin can also be used to replace portions of diseased or damaged vascular or nonvascular tissue substrate such as esophagus, pericardium, lung plura, etc. The laminated biomaterial can also be used as a skin layer replacement, for example, in burn or wound treatments. As such, the laminated biomaterial serves as a permanent dressing that acts as a scaffolding for epithelial cell regrowth. The laminated biomaterial can include antibiotics, coagulants or other (drugs desirable for various treatments that provide high local concentrations with minimal systemic drug levels. A drug can be incorporated into the biomaterial thereby decreasing the need for systemic intravenous or oral medications. The laminated elastin biomaterial can be deployed with a dye on the tissue side and then fused with the appropriate wavelength and laser energy.

Furthermore, a drug can be incorporated into the layer of elastin and/or elastin biomaterial and/or tropoelastin thereby decreasing the need for systemic intravenous or oral medications. Also, photodynamic therapy drugs ("PDT") which are activated with light can be employed herein.

Elastin Patch can be created from porcine aorta. After harvesting, it was preserved in 80% ethanol for 72 hours, then it was fully digested by soaking in 0.5M NaOH at 90 degrees centigrade with sonication. The digested aorta is cut into 4×4 cm patches. Two patches were then pressed together at 121 degrees centigrade for 15 minutes to form one bilaminar Elastin Patch. The bilaminar Elastin Patch was then packaged and sterilized at 121 degrees centigrade for 15 minutes.

Biodegradable Cyanoacrylate Glue was provided by Poly-Med, Inc. of Anderson, S.C. The glue comprises a Gel composition of Methoxypropyl Cyanoacrylate ("MPC"), and L1 (Copolymer of lactide, glycolide, and caprolactone). Cyanoacrylate adhesives are described in U.S. Pat. No. 5,350,798.

Figure 2:
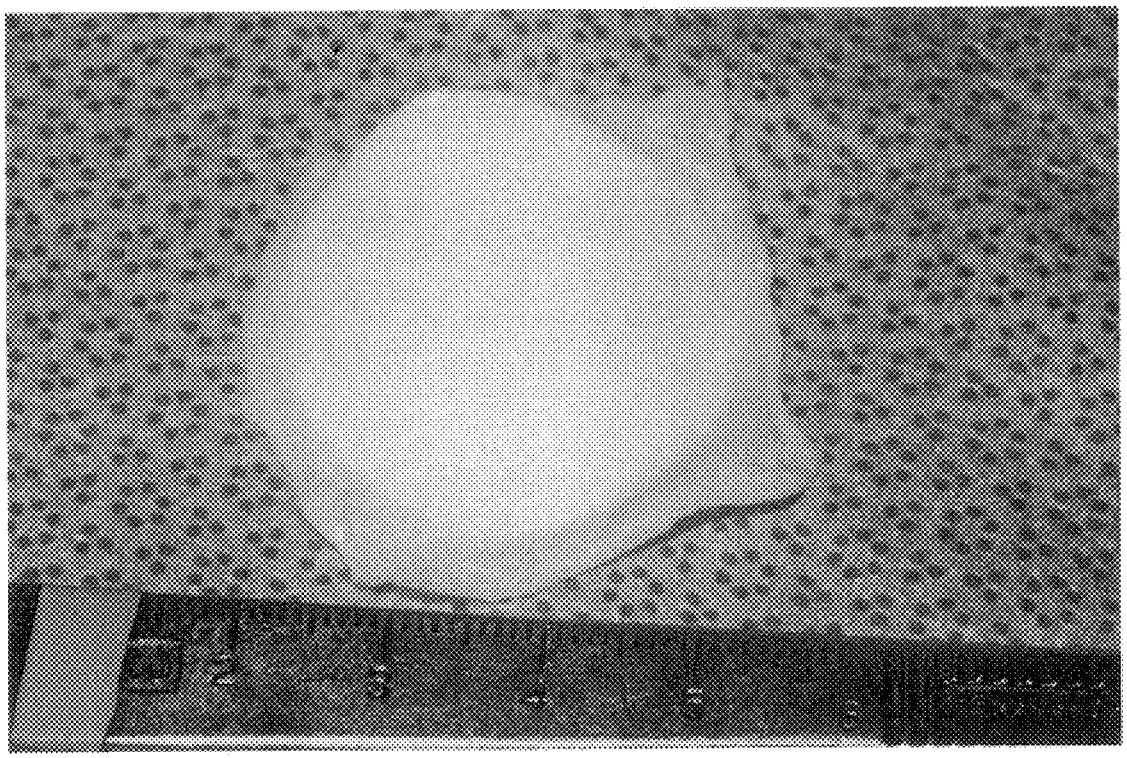
FIG. 2 is a photographic representation of a laminated Elastin/SIS composite patch of FIG. 1.
Figure 3:
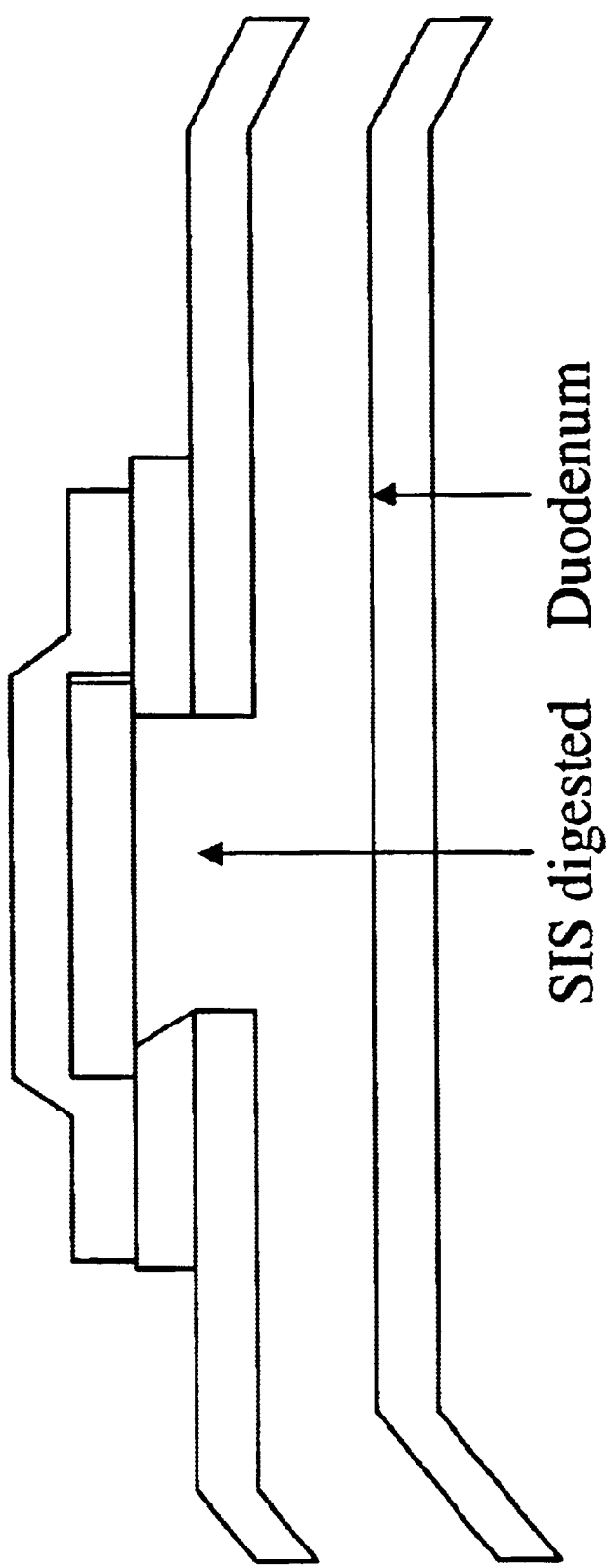
FIG. 3 is a schematic representation of the laminated Elastin/SIS composite patch of FIG. 1 applied to an opening in a Duodenum.
Figure 5:
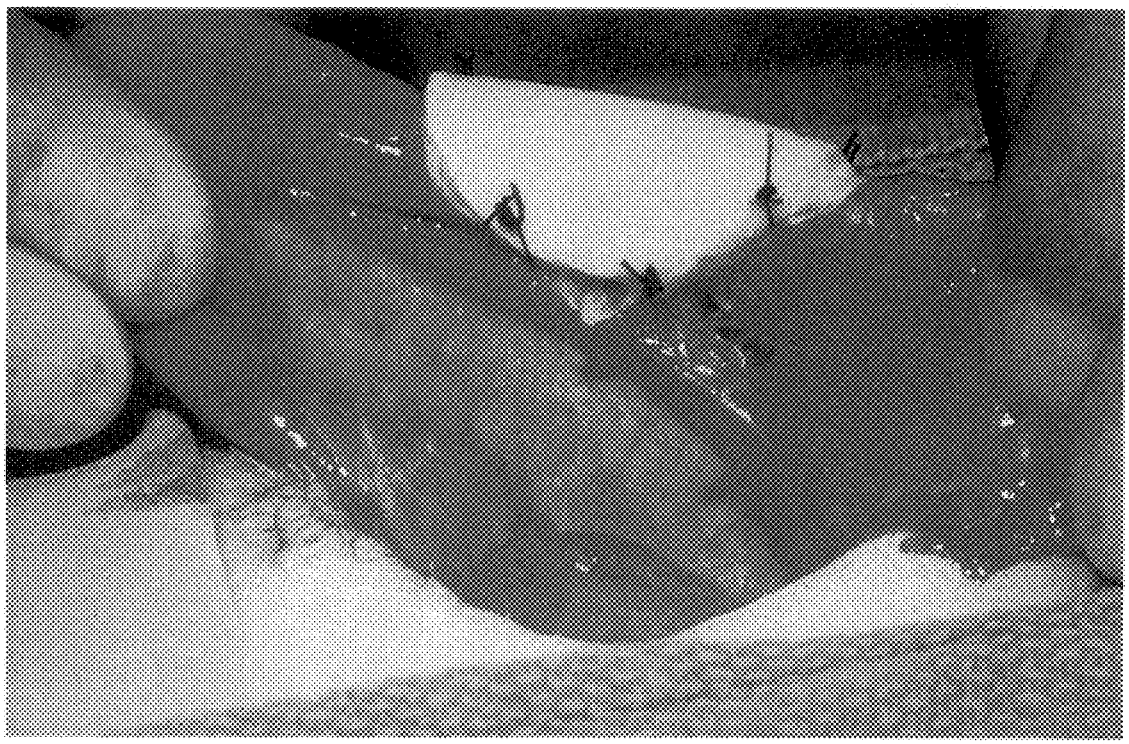
FIG. 5 is a photographic representation of a laminated Elastin/SIS composite patch applied to the duodenum.
Figure 6:
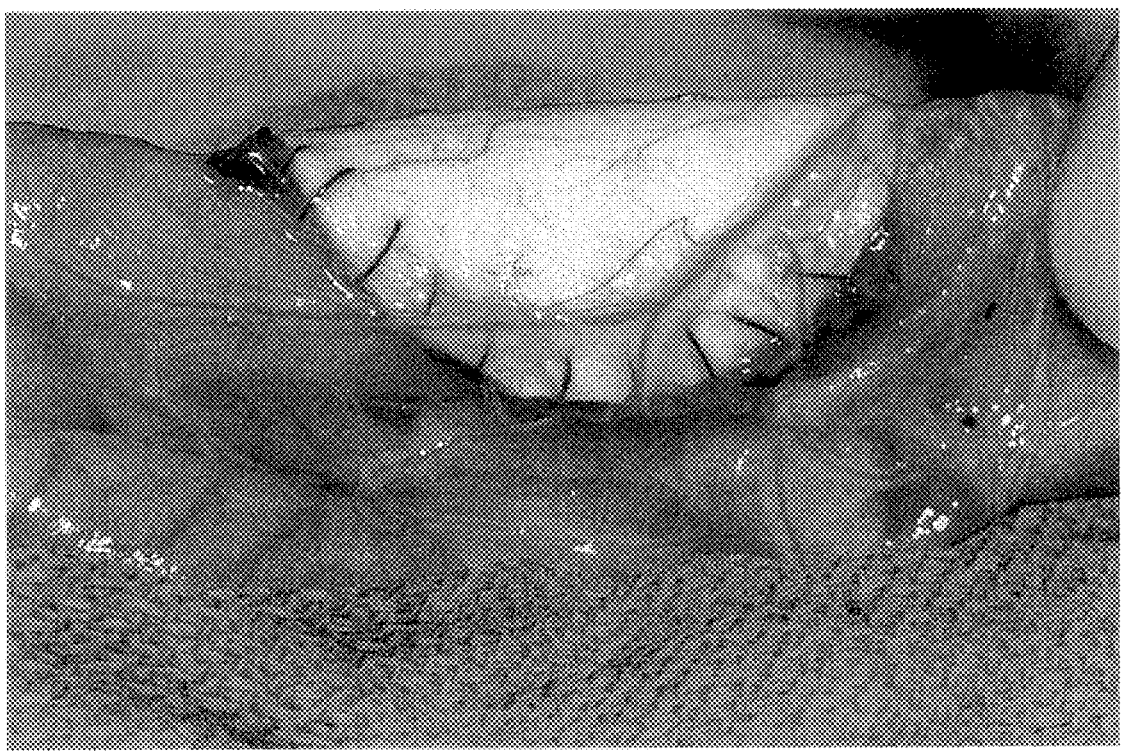
FIG. 6 is a photographic representation of the Elastin/SIS composite patch applied to the Duodenum, wrapped with the Omentum.

In a series of experiments, twenty four domestic pigs were anesthetized, intubated, and under sterile technique, underwent celiotomy. The second portion of the duodenum was mobilized, and was brought out of the wound. A circular defect of 2 cm in diameter was made on the second portion of the duodenum, excising half of its circumference. A circular Elastin Patch with a diameter of 3 cm was sandwiched between 4×4 cm of SIS sheet using biodegradable Cyanoacrylate glue (FIGS. 1, 2). This Patch was placed over the duodenal defect using the same glue (FIGS. 3, 4), and a few interrupted sutures were used to anchor the patch in place to avoid migration of the patch in case the glue fails (FIG. 5). This was further covered by omentum to provide vascular supply to the area of repair (FIG. 6). Celiotomy was closed, anesthesia was withdrawn, and the pig was extubated. The pigs were allowed to resume regular feeding soon after surgery, typically within the first hour after extubation. They were followed by clinical observation, weight gain, endoscopic studies, and Barium Swallow studies. Two to five months after surgery, the pigs were sacrificed to obtain the specimen, which were submitted for histological examination. No antibiotics or antacids were given after surgery. Animal experiments were conducted strictly following the guidelines set by the Institutional Animal Care and Use Committee of the Oregon Health Sciences University.

Twenty four domestic pigs were anesthetized and underwent celiotomy. A 2 cm circular defect was created at the second portion of the duodenum by scissors, excising half of its circumference. The Elastin Patch, combined with SIS was applied to cover the defect using biodegradable cyanoacrylate glue and a few sutures. It was then covered with omentum.

Animals were followed by weight gain, endoscopic evaluation, and upper GI Barium studies. After 2–5 months, animals were sacrificed to obtain specimens. One failed in 3 days due to a technical problem, and one failed in 20 days due to an abdominal abscess. All other 22 animals (22/24, 91.7%) did well, gaining weight. Early endoscopic studies showed an intact patch.

Figure 7:
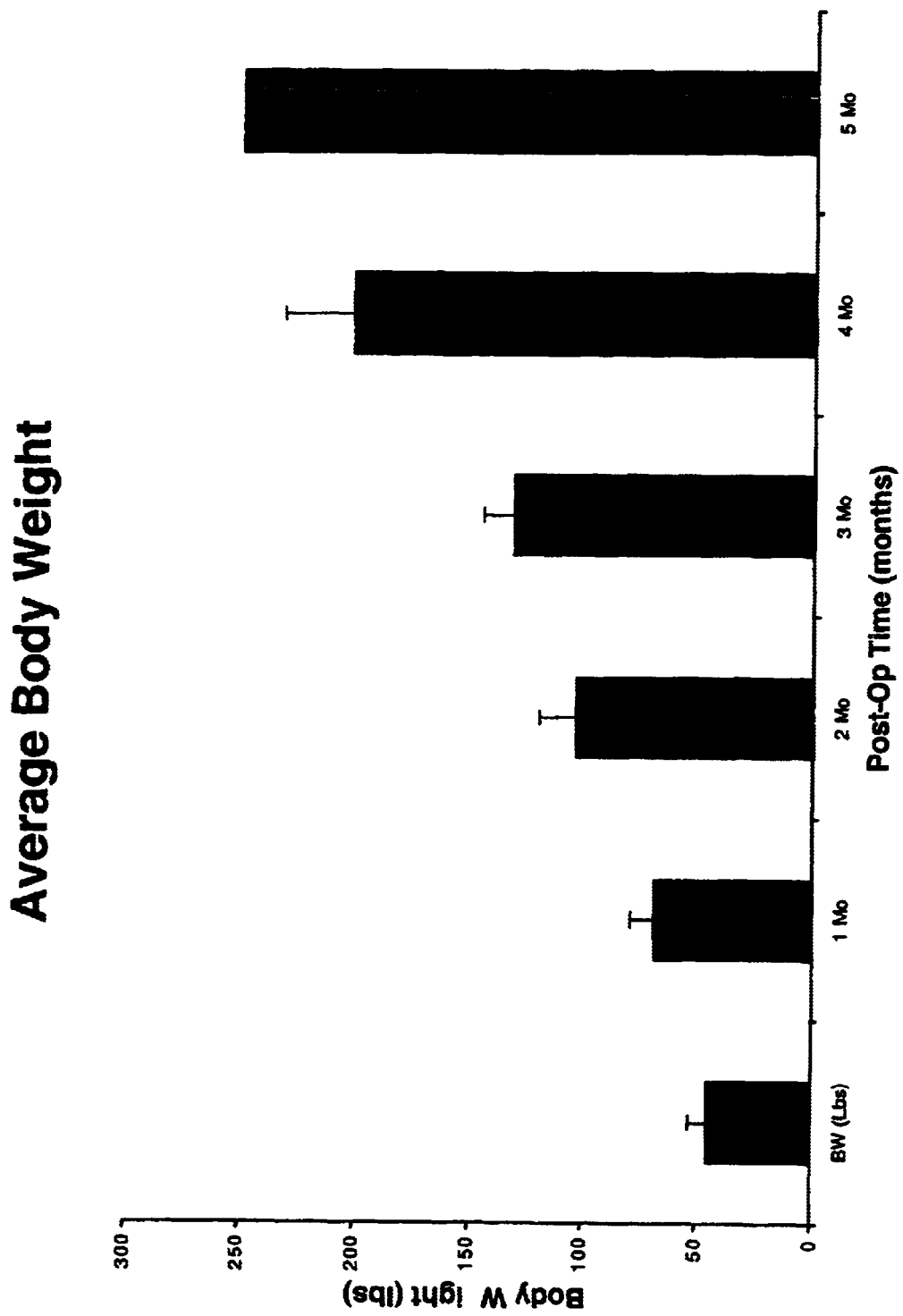
FIG. 7 is a chart showing average body weight of the experimental animals.

Upper GI studies showed varying degree of stenosis at the repair site at 3–4 months. Sacrifice after 2–5 months showed complete healing of the defect, and dissolved patch. One animal had to be sacrificed at three days after surgery. The patch has already partially dehisced with free leakage of the bowel content. This was most likely due to technical problem, failing to glue that area of the patch. Another animal had to be sacrificed at three weeks after surgery. This animal developed an abscess confined to retroperitoneal space, due to what appeared to be a perforation through the repaired site. The duodenal defect was still two centimeters in diameter, covered with thick fibrous tissue, which had a perforation leading into the abscess cavity. Fragments of Elastin were observed within the fibrous scar. The internal surface of the scar was covered with a thin layer of regenerated mucosa. The remaining twenty two animals did very well, giving the success rate of 91.7% (22/24). They were able to resume oral feeding within the first hour after surgery. They were gaining weight following the normal growth curve of domestic pigs (FIG. 7). One animal was sacrificed at seven weeks, one at two months, eleven at three months, seven at four months, and two at five months.

Figure 8:
FIG. 8 is an endoscopic view of the laminated duodenal patch repair site 5 days after the implant.

Endoscopic study was performed at one and two weeks after surgery. The laminated patch was easily identified in the second portion of the duodenum, occupying up to half its circumference. The duodenum was easily inflatable by injecting air, easily allowing the endoscope to pass through the area of repair, suggesting no mechanical obstruction (FIG. 8).

Figure 9:
FIG. 9 is a photographic representation of a duodenum 2 weeks after a repair using the laminated Elastin Patch in which a Barium study was conducted.

Upper GI contrast studies were also performed to evaluate the function of the duodenum. Early after surgery (one to two weeks), the repair site showed flat stiffening, but no significant stricture or obstruction to the passage of contrast (FIG. 9). Late studies (more than two months after surgery) showed varying degree of stricture of the repair site.

Figure 10:
FIG. 10 is a photographic representation of the gross specimen of the duodenum three months after the repair.

Gross specimen of the sacrificed animals showed complete healing of the repair site with mucosal coverage as early as seven weeks, which appeared like a healed ulcer. There were varying degrees of hypertrophic circular tissue substrate around the center of healing, causing mechanical obstruction, which seems to start resolving after five months (FIG. 10).

Figure 11:
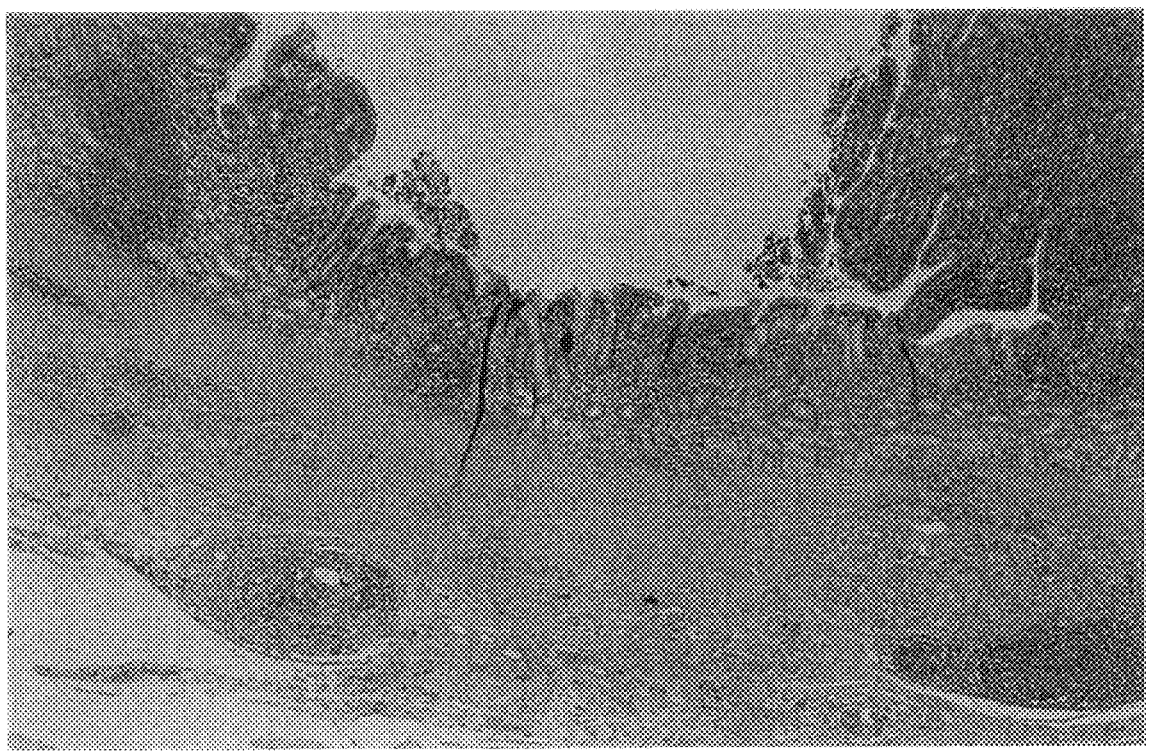
FIG. 11 is a photographic representation of the histology of a healed repair site after three months.

Histology of the specimens after 7 weeks showed a completely healed duodenal wall with mucosal regeneration in the center (FIG. 11). Submucosal tissue substrate has also regenerated with incomplete regeneration of the muscular layer. Nerves were also found in the center of the regenerated tissue substrate. Submucosal tissue substrate showed marked hyperplasia around the regenerated tissue substrate, which corresponds to the hypertrophic circular tissue substrate on the gross specimen. There was no remnant of the Elastin Patch or SIS identified in the specimen.

Major duodenal injury with significant tissue loss is a serious injury, which is very difficult to manage. It requires innovative surgical techniques, and has high morbidity, as mentioned previously. In treating a trauma victim with penetrating injury to the duodenum, which most likely has coexisting serious associated injuries, such as to liver, pancreas, great vessels, and other bowels, the chances of survival is expected to improve when a surgeon can perform a more definitive and reliable repair in a short amount of time. Primary repair is feasible only in relatively small injuries. Duodenal exclusion technique still leaves bile and pancreatic excretions to drain through the duodenal defects causing chronic fistulas. The chronic fistulas will cause electrolyte imbalance, indigestion due to non physiologic state of the GI tract, and possible intraabdominal abscess and sepsis. Although the mortality has decreased recently, owing to improvement in intensive care and antibiotics, the morbidity and cost of care remains high, and patients suffer prolonged disability. More definitive procedures such as Pancreaticooduodenectomy are too extensive for most of the critically injured patients, and will not be tolerated. Jejunal patch and duoneno jejunostomy will require long operating times. It is feasible only when the victim has intact jejunum, and it involves additional bowel resection and anastomosis.

The duodenal laminated patch repair which was developed can be performed very easily, quickly, and reliably. The Elastin Patch is designed to provide a reliable barrier for one to two weeks while tissue substrate growth and regeneration into SIS takes place. This new regenerated tissue substrate will, in turn, serve as an effective barrier, while remaining elastin is completely digested in four to six weeks. Because the subject Elastin Patch itself is biodegradable by digestive enzymes in the duodenum, the risk of immunological response and infectious complication of the patch is minimal. SIS is well integrated in the regenerated tissue substrate, and eventually disappears. This material, which is almost pure collagen, is an excellent scaffold for tissue growth.

Figure 12:
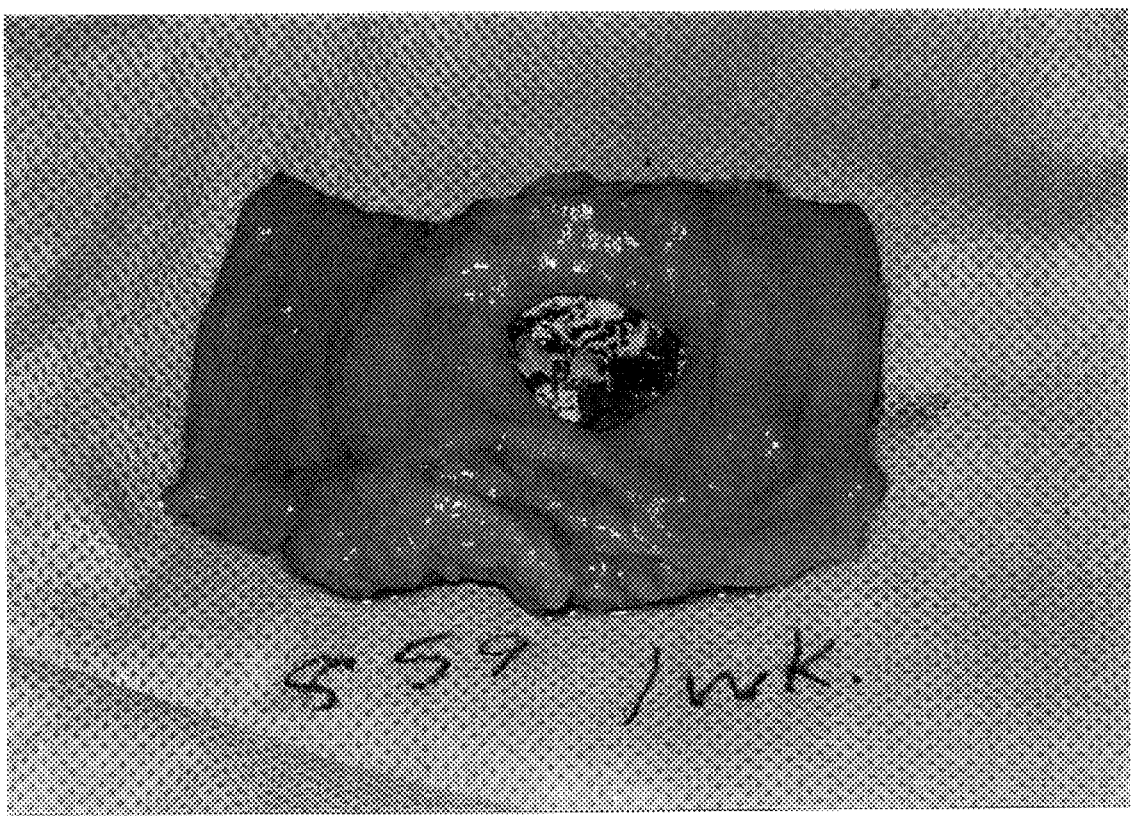
FIG. 12 is a photographic representation of the gross specimen of the duodenum, one week after the repair, the SIS and dyed glue inside the laminated elastin having been digested.

It is believed that the SIS inside the Elastin is completely digested by duodenal content within a few days (FIG. 12). Elastin on the other hand, is much more durable, and serves as an effective barrier for two to four weeks.

The biodegradable cyanoacrylate glue was used in order to simplify the operative repair and to provide an immediate watertight seal against the duodenal enzymes. One critical problem we faced with our pure Elastin Patch was that the material was quite fragile, lacking in mechanical strength. Although not impossible, it was quite technically demanding to place a suture through this material without laceration. Placing this laminated patch with glue made it much simpler and easier, and initial mechanical strength of the tissue fusion was quite satisfactory.

Figure 13:
FIG. 13 is a photographic representation of the histology of the repair site of an animal 20 days after the repair.

Two animals did not survive the long term experiment. One of them never regained GI continuity after surgery, and had to be sacrificed after three days. There was a leak at the distal medial corner of the Elastin Patch, and this was most likely due to a technical failure. We either failed to apply the glue in this corner, or failed to apply the Elastin Patch before the glue dried out. The original glue had no color and was transparent, but later a dyed glue was used to visually identify the glued area. The other animal started to deteriorate two weeks after surgery, losing appetite and body weight. At sacrifice on the twentieth day, we found that the animal had developed a retro peritoneal abscess. The area of defect was covered with thick fibrous tissue substrate, which had a 3 mm hole connecting to the abscess cavity. Histology showed fragments of elastin in the fibrous scar, and the inner surface was covered with thin regenerated mucosa (FIG. 13). This animal had a relatively large hole in the duodenum, and inadequate tissue fusion between the bowel edge and the patch was felt to be the cause of early dehiscence.

The subject patch is virtually made of pure elastin without impregnation of any enzyme inhibitors or antibiotics. Preliminary study to test its resistance against hydrochloric acid in vitro showed no degeneration after one week. Duodenal content, however, is mixture of bile, pancreatic enzymes, hydrochloric acid, ingested food, and microorganisms. Pancreatic digestive enzymes, such as elastase, could rapidly degenerate the Elastin Patch.

Whereas enzyme inhibitor, Elgin C, strongly inhibits the solubilization of human aortic elastin by human pancreatic elastase, the efficacy of the inhibitor sharply decreases if elastase is reacted with elastin for prolonged time. Surgical experiments were typically performed in thirty minutes from skin to skin. The actual time required for duodenal repair itself was less than fifteen minutes. No other bowel resection or anastomosis is required, and our animals can resume oral feeding immediately after they recover from anesthesia. For trauma victims with penetrating injury to the duodenum this is an ideal treatment in that the surgery time is minimal and recovery is fast, eliminating the need for prolonged hospitalization with antibiotics and intravenous hyperalimentation.

A major concern with this repair was late stricture of the repair site. In our experience, it seems to heal by both regeneration and contraction, leaving a mild to moderate degree of stenosis, but not as severe as one would expect from healing by contraction alone. The center of the healed scar showed evidence of mucosal regeneration. There was always a circular ridge of hypertrophied mucosa or submucosal tissue substrate around the center, which also seems to contribute to the mechanical constriction of the duodenal lumen. This was most prominent at three months, and the two animals after 5 months showed tendency of resolution, although objective quantification was not possible.

It is assumed that this is caused by the early degeneration of the glue, which allows the glued edge of the duodenum to fall into the lumen, exposing this part to the duodenal content. This circular edge will undergo inflammatory changes, resulting in hypertrophied circular scar. The glue (GF 62) is composed of Methoxypropyl Cyanoacrylate (MPC), and L1 (Copolymer of lactide, glycolide, and caprolactone). Methoxypropyl Cyanoacrylate with other modifiers result in higher adhesive strength than isobutyl cyanoacrylate when used to approximate soft tissues. The use of cyanoacrylate glue to repair the injury may be also contributing to resistance against infection.

The Elastin Patch provides a reliable barrier to repair major tissue substrate defect in the second portion of the duodenum. By combining this patch with SIS, we could obtain a fairly strong material, which is resistant to infection and digestive enzymes, while allowing the tissue substrate to heal from outside.

The modified cyanoacrylate glue provides quick and easy water tight tissue fusion for the patch. Further modification to prolong its function over two weeks is desired, which is likely to reduce the degree of stricture at the repair site.

Figure 16:
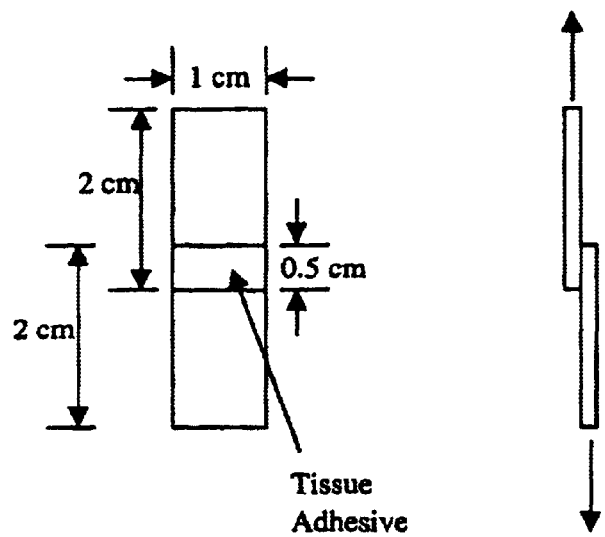
FIG. 16 is a further pictorial representation of the breaking strength of GF-62 lap welds on pressed aortic heterografts in both neutral and alkaline solutions.

Regarding tissue adhesive testing, porcine aorta heterografts of pure elastin were cut length wise and unfolded into a rectangular sheet of tissue substrate. This 5 cm×6 cm sheet was pressed between two glass plates, immersed in a water bath, and then placed in the autoclave at 121 C. for 15 minutes. Each heat pressed sheet was cut down the middle into two halves. The halves were then overlapped and glued together using GF 62 adhesive. This was allowed to cure overnight in a moist environment. After curing, each glued sample was cut into multiple 1 cm×6 cm strips using a razor blade (FIG. 16). These samples were immersed in either a bath of PBS as the control or Sodium Phosphate with a pH of 8.6 for a specified time and then pulled with the Chatillon V1000 past the breaking point. The strength was calculated as the breaking load per glued area. Three samples were used for testing at each time point for each pH condition.

Figure 4:
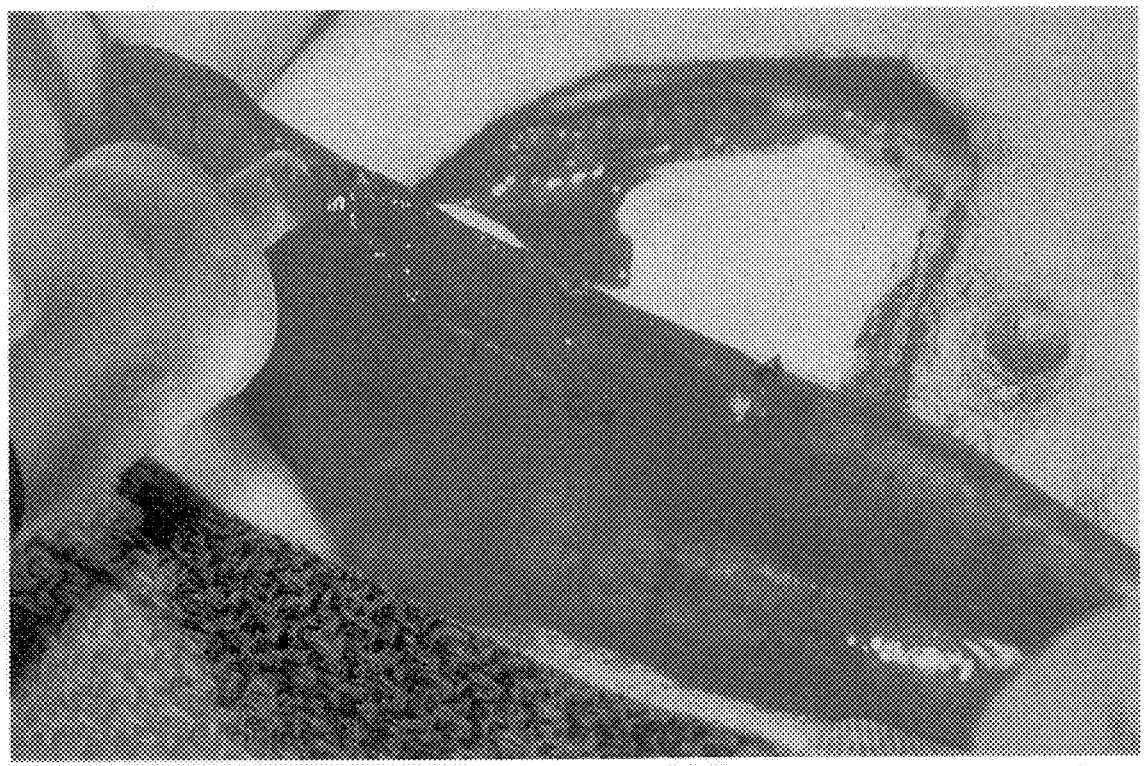
FIG. 4 is a photographic representation of the 2 cm opening in the duodenum and application of a glue as an adhesive.

The results of the shear strength tests are shown in FIG. 4. The control sections in PBS were only performed for 4 days and show very little change in breaking strength. The sections in the alkaline solution increased in strength to a maximum at 95 hours and maintained this strength until the last time point at 230 hours. The alkaline environment of the duodenum is not causing the glue to degrade prematurely.

Studies in this segment focused on (1) preparing several candidate absorbable cyanoacrylate based compositions (Compositions Nos. GF 70, GF 72, GF 74, GF 76, and GF 77) with improved adhesive strength retention for screening of the different candidate formulations; (2) incorporating a safe dye into the cyanoacrylate based tissue adhesives (Compositions GF 71, GF 73, GF 75, GF 62D, GF 76D, GF 77D and GF 78D) without compromising their shelf lie and in vivo performance; (3) preparing, reproducibly, sufficient amounts of most promising tissue adhesives for evaluation (Compositions Nos. GF 62, GF 62D and GF 72D); (4) preparation of a series of highly absorbable tissue adhesives with expected high compliance as cured films for evaluation in low load bearing applications (Compositions Nos. HD 1, HD 2, HD 3 and HD 4); and (5) incorporating ground elastin and chopped PGA fibers in absorbable tissue adhesives for use as a hemostatic bandage (Compositions Nos. HB 1, HB 2 and HB 3).

Two new test methods, the nylon film and fabric cleavage test were developed and compared with the goat skin test method previously developed. Of the three methods, the fabric cleavage test was identified as the most reliable screening method.

Figure 14:
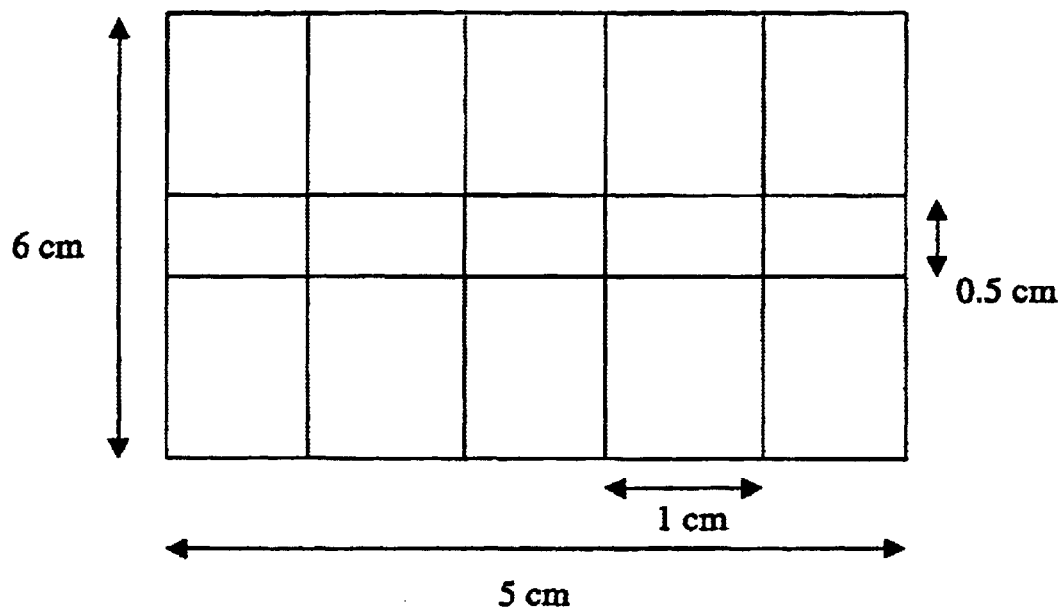
FIG. 14 is a pictorial representation of shear tests of lap welds using tissue adhesives on elastin aortic patches.
Figure 15:
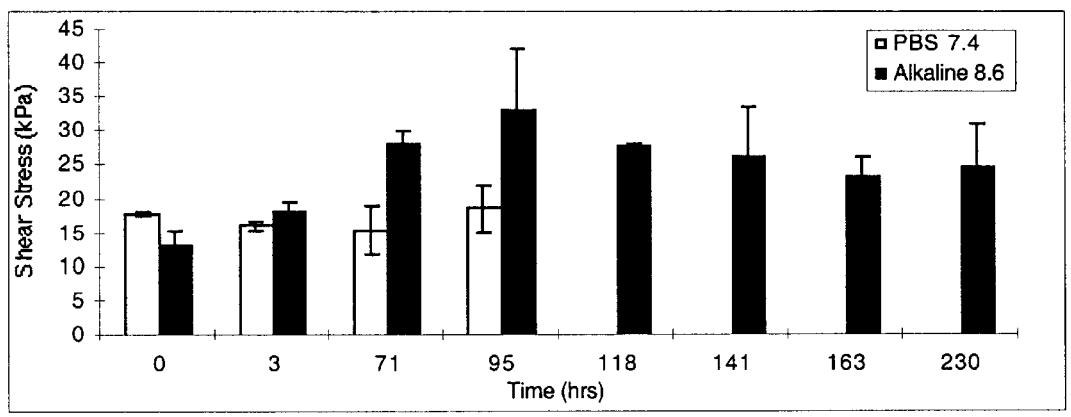
FIG. 15 is pictorial representation of the breaking strength of GF-62 lap welds on pressed aortic heterografts in both neutral and alkaline solutions.

The shear tests are conducted on 1.0 cm×2.0 cm pressed porcine aortic Elastin Patches. Each piece is overlapped by 0.5 cm as indicated in FIG. 14. The tissue adhesive is allowed to cure for 3–4 hours at which time the pieces are pulled apart on the Chatillon V1000. The flexibility tests are conducted on a 1.0 cm×2.0 cm pressed porcine aortic Elastin Patch by pre stretching the piece and then coating one side with tissue adhesive. The tissue adhesive is allowed to cure for 3–4 hours at which time the pieces are pulled apart on the Chatillon V1000. The change in the initial slope of the load/displacement curve is an indication of the effect of the tissue adhesive on the elasticity of the Elastin Patch. The results of the shear strength tests is shown in FIG. 15. The adhesives are of equal or greater strength than the SuperGlue, which was used as a control. Both GF 51 and GF 62D had the smallest effect on flexibility, while SuperGlue greatly decreased the elasticity of the Elastin Patch.

Bilateral vertical neck incisions were made in a 80 lb. domestic swine. A surgical dissection proceeded down to the level of the carotid and jugular veins. The jugular vein was retracted laterally and the underlying carotid arteries were exposed. 5000 units of heparin were given intravenously and the right carotid artery was isolated proximally and distally. Due to lack of adequate vascular clamps a hemostat was used to occlude proximal carotid flow. An 4 cm section of the right carotid artery was excised and an appropriately sized tubular carotid heterograft was brought onto the field. A running continuous suture of 7-0 Prolene was then used to secure the proximal anastomosis. The suture line was secured and the distal portion of the elastin graft was occluded with finger pressure. The proximal carotid hemostat clamp was then released allowing the elastin graft to be fully pressurized. The graft itself tolerated the pressurization well, however at the anastomotic site, there was significant leakage from the needle holes. In addition after approximately 5 minutes the needle hole sites started to break down, eventually leading to a complete circumferencial tear of the elastin graft at the anastomotic sight.

The carotid artery was reclamped and a second elastin graft brought onto the field This graft was prepared by painting a thin coating of PS MPC cyanoacrylate glue (Poly-Med, Inc.) onto the outside of the graft covering approximately 5 mm. of each end. The glue was allowed to cure for 2 minutes. The glue coated graft had much greater tear strength which assisted anastomotic stabilization. Anastomosis was then completed with running a continuous suture of 7-0 Prolene from the proximal carotid artery to the treated elastin graft. Upon releasing the clamp the suture line held tight with minimal to no leakage. Again the elastin graft pressurized normally. The distal end of the graft was then similarly treated in a distal anastomosis was created to the distal carotid artery with a running suture of 7-0 Prolene in a similar fashion to the proximal anastomosis. The hemostats were then removed and the graft was allowed to perfuse. The graft remained pulsatile and perfusing for over an hour, however as the Heparin wore off (and most likely due to the proximal carotid arterial injury secondary to the hemostat) the carotid artery proximal the graft began to thrombose. This is certainly due to iatrogenic injury caused by the unavailability of the appropriate vascular clamp.

A scanning electron micrograph of the lumenal surface of the heterograft is depicted. A vigorous thrombgenic response is absent from the surface of the graft. Occasional platelets and scattered red blood cells with protein adsorption and mild fibrin adhesion. The heterograt was easy to handle, but was tactically difficult to deploy without the addition of the PS MPC glue which served as backing able to withstand the tearing force of the sutures. Work is underway to develop a cross bilaminated carotid heterograft with increased tear strength using the heat pressing technology developed for the aortic heterografts.

Poly-Med Inc. (Anderson, S.C.) provided cyanoacrylate tissue adhesives (HAF) to evaluate using Elastin Patches to repair lung and liver lacerations. Fresh porcine lungs with trachea intact were trimmed of extraneous tissue substrate and kept on ice. A puritan manual resuscitator was attached to the trachea and the lungs were inflated with air. A 1×3 cm resection of the right upper lobe was discovered HAF 3 adhesive was dispensed from a micropipette around the circumference of the patch. The Elastin Patch was placed over the lesion, pressed gently into place, and allowed to cure. After 2 minutes the lungs were inflated and the right upper lobe was airtight. Next, a 1.5 cm incision, 1 cm deep, was cut with a scalpel into the right lower lobe, which was previously fully inflated. Haf 3 tissue glue was applied to the surface of the lung with a micropipette and spread around the incision with a glass tube. An Elastin Patch was placed over the incision, pressed gently into place, and allowed to cure creating an airtight seal. The Elastin Patches were tested for leaks after three hours. Both Elastin Patches developed small air leaks which were attributed to the glue cracking from excessive brittleness.

Elastin Patches were glued to a porcine liver with HAF 3 tissue adhesive to evaluate the feasibility of using an elastin liver patch to repair liver lacerations. A 1.5 cm incision, 1 cm deep, was made on the liver. HAF 3 tissue glue was applied to the surface of the liver via a micropipette and spread around the incision with a glass tube. A single layer heat pressed aortic elastin graft was placed over the lesion, pressed gently into place, and allowed to cure for 3 hrs.

Strips of Elastin Patches were glued to the serosa of porcine lung and the surface of liver with HAF tissue adhesives and tested for adhesive strength. Fifteen microliters of glue was deployed via a micropipette onto the surface of lung and liver strips. A 1 cm wide strip of single layer heat pressed aortic elastin was pressed gently into place and allowed to cure for a minimum of 10 minutes. Bonded specimens were mounted on a uniaxial tension tester and pulled apart until bond failure. Sample numbers were too small for statistical comparison between glue prototypes. Average shear strengths were as follows: lung patch=55.0+/18.0 grams (n=5); liver patch=92.0+/18.0 grams (n=3).

Experimental new surgical repair of highly morbid duodenal injury using Elastin Patch and Biodegradable Cyanoacrylate. Of all the gastrointestinal tract injuries, such as with the gunshot wound in the battle field, loss of duodenal tissue substrate from its second portion is extremely difficult to repair, due to its anatomical structure with its close attachment to the head of the pancreas and connections with the biliary tree and pancreatic duct, which precludes resection with end to end anastomosis. Unless the injury is a single small defect, simple repair is not possible in this region. Primary suture closure of a large defect will compromise the lumen of the Duodenum, creating stricture and obstruction.

Major loss of tissue substrate in this region requires innovative techniques, such as:

1) Diverticularization of the duodenum
2) Duodenal exclusion with gastrojejunostomy
3) repair with roux en Y duodenojejunostomy
4) Pancreaticoduodenectomy (Whipple A procedure)

First two procedures are accompanied by prolonged external drainage of the duodenal content, which makes it extremely difficult to manage fluid and electrolyte imbalance, and high incidence of intra abdominal infection, sepsis, and chronic fistula formation, predisposing the victim to prolonged intensive care, hospitalization, and disability. This is due to the high content of electrolyte and digestive enzymes in the duodenal fluid, which comes mainly from pancreatic juice and bile. The pancreatic exocrine enzyme, Trypsin is excreted in inactive form, Trypsinogen, which is then activated by duodenal mucosal Enterokinase. The activated Trypsin will further activate other pancreatic exocrine enzymes excreted in inactive form, such as, Chymotrypsin, Elastase, Kallikrein, and Carboxypeptidase A & B. As a result, prolonged leakage of duodenal content is associated with prolonged and extensive tissue substrate loss and sepsis. Recent development in antibiotics and intensive care has significantly reduced the mortality rate from this condition, but morbidity is still high.

The third procedure is feasible only for limited amount of tissue substrate loss that can be covered by the jejunum, plus it requires another bowel anastomosis. Prolonged procedure in an acutely injured patient, with multiple other problems, will increase the mortality. This is also feasible only when intact jejunum is available.

The fourth procedure is very extensive, including the excision of the head of the pancreas, as well as in the common bile duct, and is indicated only when both common bile duct and pancreatic duct, as well as the duodenum, are involved in the injury. Very often, in the case of major trauma, the victim with an unstable condition from another injury, hypothermia or shock cannot tolerate this procedure.

The Elastin Patch developed is used to repair defects in the duodenum without compromising the lumen, need for other bowel anastomosis, or extensive resection. This material acts as a skelton of native tissue growth, such as duodenal mucosa and serosa, to eventually cover the defect, while providing mechanical barrier for the bowel content to avoid fistula formation. The material is acid resistant in vitro, and is potentially resistant to various digestive enzymes and infective organisms.

A sacrificed animal showed excellent fusion of the patch after 30 seconds. In order to evaluate the use of elastin heterografts in repair of duodenum with their exposure to duodenal contents, an Elastin Patch of elastin heterograft was placed on defect created at the second portion of duodenum. An adult mini swine around 30 lbs. was sedated after 24 hours of starvation, intubated and underwent general anesthesia with Isoflurane. One dose of prophylactic antibiotic was given intramuscularly (Cefotetan 500 mg). The animal was placed in supine position. The abdominal wall was sterilized with betadine and draped in a sterile fashion. A 5 cm long horizontal incision was made on right upper quadrant, just below the right second nipple, then the abdominal wall muscle and fascia were divided using electrocautery, and the peritoneal space was entered. The second portion of the duodenum was exposed just below the incision. A full thickness defect 2 cm in diameter was created at the center of the second portion of duodenum with scissors, hemostasis was achieved using electrocautery, and defect was closed with the elastin heterograft patch using a biodegradable cyanoacrylate. The area of Elastin Patch repair was covered with omentum using a few interrupted sutures. Abdominal wall was closed in layers. Polysporin ointment was applied to the incision line.

Twenty four hours after the surgery, the pig recovered well, tolerating oral diet, with normal activity. Five days after surgery, the pig continued to eat well. The animal was inspected in the cage, and it was encouraging to learn that all the food was consumed, with no evidence of emesis, and a large amount of stool was present in the cage. The animal appeared to have been in full normal activity. An endoscope was performed to visualize the duodenum. The stomach was nearly empty after 24 hours of fasting, suggesting good emptying. The patch was occupying about ⅓ of the circumference, and was found to be intact. The mucosal edge had minimal inflammatory reaction. The duodenum had widely patent lumen with no stricture. The duodenum was easily inflatable, and there appeared to be no leak. Several photographs were obtained.

In order to evaluate the use of an Elastin Patch heterograft in the repair of a duodenum with exposure to duodenal contents, an Elastin Patch heterograft was placed on a defect created at the second portion of a duodenum. A domestic swine around 30 to 40 pounds was sedated after fasting for 24 hours, intubated and underwent general anesthesia with Isoflurane. One dose of prophylactic antibiotic was given intravenously (Cefotetan 500 mg).

The animal was placed in the supine position. The abdominal wall was sterilized with Betadine, and draped in a sterile fashion. A 5 cm long horizontal incision was made on the right upper quadrant, just above the right second nipple, then the abdominal wall muscle and fascia were divided using electrocautery, and the peritoneal space was entered. The second portion of the duodenum was exposed, mobilized, and brought out of the incision. A full thickness defect of 2 cm in diameter, which was about half of the circumference was created at the center of the second portion of the duodenum with scissors. Hemostasis was achieved using electrocautery, and the defect was closed with the Elastin Patch heterograft patch using a bioabsorbable cyanoacrylate (GF-62).

The area of patch repair was covered with Omentum using a few interrupted sutures. The abdominal wall was closed in layers. Antibiotic ointment was applied to the incision line. No oral antibiotics or anti acids were given after surgery. The follow up was done by clinical evaluation of the animal, as well as endoscopic and Barium Swallow studies.

recovered well, tolerating oral diet, with normal activity. 5 days after surgery, the pig continued to eat well. The animal was inspected and all the food continued to disappear, with no evidence of emesis, and large amount of stool. The animal was in full normal activity. An endoscopic procedure was performed to visualize the Duodenum. The stomach was nearly empty after 24 hours of fasting, which suggested good emptying. The patch occupied about ⅓ of the circumference, and was found to be intact. The mucosal edge had minimal inflammatory reaction. The duodenum had a widely patent lumen with no stricture. The duodenum was easily inflatable and there was no leak.

An endoscopic procedure was repeated to follow up. The Elastin Patch was found to be dehisced. The pig started vomiting that morning. The pig was sacrificed and found that the Elastin Patch was completely dehisced. Histology showed some mild degeneration of the Elastin Patch with no tissue substrate in growth.

In Case 2, bioabsorbable cyanoacrylate glue (GF 62) was used with a bilaminar pressed Elastin Patch to enhance the durability. To enhance tissue growth around the Patch, SIS patches were added. The pig started eating soon after surgery, and resumed normal activity by the next day. A Barium Swallow study was performed after surgery. The animal weighed 65 lbs., gaining 34 lbs. since surgery. There was no dilatation of the proximal duodenum. The area of Elastin Patch looked smooth, with good motility, without obstruction. There was no leak. There was an area just proximal to the Elastin Patch, that showed some difficulty in dilating with peristalsis, but eventually the Barium passed through. This might indicate some kink of the proximal duodenum due to the adhesive. The animal continues to do well.

TABLE 1

Results

| Case # | Pig # | Op date | BW #1 | Patch | Glue | Suture | Endoscope | #1 BS date | Status | Outcome |
|---|---|---|---|---|---|---|---|---|---|---|
| 1 | GI 001 | Jul. 1, 1998 | 35 | PE | GF-52 | Yes | 5, 12 days | n/a | Sac 7/13 | Deh Patch |
| 2 | 741 | Aug. 19, 1998 | 35 | S/DE/S | GF-62 | Yes | | 9/22 | 69 lbs | alive |
| 3 | 734 | Aug. 26, 1998 | 50 | S/DE | GF-62 | Yes | | 9/22 | 75 lbs | alive |
| 4 | 745 | Sept. 3, 1998 | 48 | S/DE/S | GF-62 | Yes | | | | alive |
| 5 | 747 | Sept. 3, 1998 | 46 | S/DE/S | GF-62 | Yes | | | | alive |
| 6 | 748 | Sept. 3, 1998 | 43 | S/DE/S | GF-62 | Yes | | | | alive |
| 7 | 767 | Sept. 11, 1998 | 40 | S/DE | GF-62 | Yes | | | | alive |
| 8 | 751 | Sept. 11, 1998 | 41 | S/DE | GF-62 | No | | | Sac 9/18 | Dehisced Patch |
| 9 | 752 | Sept. 11, 1998 | 48 | S/DE | GF-62 | No | | | Sac 9/21 | Dehisced Patch |
| 10 | 779 | Sept. 21, 1998 | 51 | S/DE/S | GF-62 | Yes | | | | alive |
| 11 | 778 | Sept. 21, 1998 | 48 | S/DE/S | GF-62 | Yes | | | | alive |
| 12 | 777 | Sept. 21, 1998 | 41 | S/DE/S | GF-62 | Yes | | | | alive |
| 13 | 797 | Sept. 21, 1998 | 43 | S/DE/S | GF-62 | Yes | | | | alive |
| 14 | 781 | Sept. 25, 1998 | 44 | S/DE/S | GF-62 | Yes | | | | alive |
| 15 | 782 | Sept. 25, 1998 | 45 | S/DE/S | GF-62 | Yes | | | | alive |
| 16 | 783 | Sept. 25, 1998 | 41 | S/DE/S | GF-62 | Yes | | | | alive |
| 17 | 784 | Sept. 25, 1998 | 41 | S/DE/S | GF-62 | Yes | | | | alive |
| 18 | 776 | Sept. 25, 1998 | 47 | S/DE/S | GF-62 | Yes | | | | alive |
| 19 | 785 | Sept. 28, 1998 | 40 | S/DE/S | GF-62 | Yes | | | | alive |
| 20 | 786 | Sept. 28, 1998 | 38 | S/DE/S | GF-62 | Yes | | | | alive |
| 21 | 787 | Sept. 28, 1998 | 49 | S/DE/S | GF-62 | Yes | | | | alive |
| 22 | 788 | Sept. 28, 1998 | 40 | S/DE/S | GF-62 | Yes | | | | alive |
| 23 | 738 | Sept. 28, 1998 | 76 | S/DE/S | GF-62 | Yes | | | | alive |
| 24 | 789 | Sept. 29, 1998 | 43 | S/DE/S | GF-62 | Yes | | | | alive |
| 25 | 790 | Sept. 29, 1998 | 46 | S/DE/S | GF-62 | Yes | | | | alive |
| 26 | 791 | Sept. 29, 1998 | 39 | S/DE/S | GF-62 | Yes | | | | alive |
| 27 | 792 | Sept. 29, 1998 | 51 | S/DE/S | GF-62 | Yes | | | | alive |

Experiment in vivo was conducted with a single Elastin Patch, using bioabsorbable cyanoacrylate glue from Poly-Med, Inc. (GF 52). 24 hours after the surgery, the pig In Case 3, using the same glue and the SIS only on the outside of the Elastin Patch, it was determined whether the Elastin Patch could tolerate the duodenal digestive enzymes, and also to see the potential for tissue growth with SIS only on the outside. A Barium Swallow was performed after surgery. The animal weighed 75 lbs., gaining 25 lbs. since surgery. The Barium passed very easily through the area of the patch, without any evidence of obstruction or leak. The pig is alive and doing very well.

Cases 4, 5, 6 were conducted using the same procedures and materials were identical to Case 2. After surgery, they are doing very well. We will perform a Barium Swallow tests were conducted and they are doing well.

Case 7, 8 and 9 had an identical procedure as the Case 3, and are doing well. Cases 8 and 9 had the same Elastin Patch (SIS on outside only) and the glue. The entire procedure was performed only with the glue, without any sutures, except for the abdominal wound closure.

Unfortunately, these animals started having problems with feeding after 6 to 7 days, and we sacrificed them on postoperative day 7 and 10. Case 8 had a dehisced patch with a leak into the peritoneal space, causing intra abdominal abscess. Case 9 had a completely dehisced patch which contained a leak within the omentum, forming a large abscess, causing duodenal obstruction and massive gastric dilatation.

The shear tests are conducted on 1.0 cm×2.0 cm pressed porcine aortic Elastin Patches. Each piece is overlapped by 0.5 cm as indicated in FIG. 15. The tissue adhesive is allowed to cure for 3–4 hours at which time the pieces are pulled apart on the Chatillon V1000. The flexibility tests are conducted on a 1.0 cm×2.0 cm pressed porcine aortic Elastin Patch by pre stretching the piece and then coating one side with 25 ml of tissue adhesive. The tissue adhesive is allowed to cure for 3 4 hours at which time the pieces are pulled apart on the Chatillon V1000. The change in the initial slope of the load/displacement curve is an indication of the effect of the tissue adhesive on the elasticity of the Elastin Patch.

The results of the shear strength tests is shown FIG. 16. The adhesives are of equal or greater strength than the SuperGlue, which was used as a control. Both GF 51 and GF 62D had the smallest effect on flexibility, while SuperGlue greatly decreased the elasticity of the Elastin Patch.

In order to evaluate the use of Elastin Patch heterograft in repair of duodenum with their exposure to duodenal contents, a patch of elastin heterograft was placed on defect created at the second portion of duodenum. Adult mini swine around 30 to 40 lbs. was sedated after fasting for 24 hours, intubated and underwent general anesthesia with Isoflurane. One dose of prophylactic antibiotic was given intravenously. (Cefotetan 500 mg)

The animal was placed on supine position. Abdominal wall was sterilized with Betadine, and draped in sterile fashion. A 5 cm long horizontal incision was made on right upper quadrant, just above the right second nipple, abdominal wall muscle and fascia was divided using electrocautery, and peritoneal space was entered. The second portion of the duodenum was exposed, mobilized, and brought out of the incision. A full thickness defect of 2 cm in diameter was created at the center of the second portion of duodenum with scissors, which was about half of the circumference, hemostasis was achieved using electrocautery, and defect was closed with the Elastin Patch heterograft using bioabsorbable cyanoacrylate from Poly-Med, Inc.

The area of patch repair was covered with Omentum using a few interrupted sutures. Abdominal wall was closed in layers. Antibiotic Ointment was applied to the incision line. No oral antibiotics or anti acids were given after surgery. The follow up was done by clinical evaluation of the animal, Endoscope, and a Barium Swallow contrast study using 27 implants were performed.

An experiment in vivo with single Elastin Patch, using Poly-Med glue. (GF 52). Within 24 hours after the surgery, the pig has fully recovered, tolerating oral diet, with normal activity. Endoscopic examination was performed to visualize the Duodenum. The stomach was nearly empty after 24 hours of fasting, suggesting good emptying. The Elastin Patch was occupying about ⅓ of the circumference, and was found to be intact. The mucosal edge had minimal inflammatory reaction. The Duodenum had widely patent lumen with no stricture. The Duodenum was easily inflatable, and there was no leak.

A repeat endoscopic exam was performed as follow up. Unfortunately, the patch was found to be dehisced. The animal care staff reported that the pig started vomiting from that morning. We sacrificed the pig and found that the Elastin Patch was completely dehisced. Histology showed some mild degeneration of the Elastin Patch with no tissue in growth.

Twenty six implants were performed. A bioabsorbable Poly-Med cyanoacrylate glue (GF 62) was used with a bilaminar pressed Elastin Patch to enhance the durability. To enhance tissue growth around the bilaminar Elastin Patch, we sandwiched it with small intestinal submucosa (SIS) patches. Also, in order to reduce the chance of mechanical trauma to the Elastin Patch, we decided not to endoscope routinely. All the pigs started eating soon after surgery, and resumed normal activity by the next day. Only glue was used for applying the Elastin Patch, without any sutures. These animals, however, had to be sacrificed at 7 and 10 days after surgery due to dehiscence of the Elastin Patch, with leak and abscess formation.

Of the remaining 24 animals, there were two early failures. One of them had a leak on the $3^{rd}$ day, and had to be sacrificed. This was most likely due to a technical problem. The other one had to be sacrificed on the 20th day due to a perforated patch. The cause of this is not quite certain. All other 22 animals survived long term. Only one animal developed a wound infection. In accordance with the animal care guideline, we electively sacrificed at 7 weeks. This animal showed no leak or obstruction of the duodenum, and the area of the patch has completely healed. Barium swallow tests were performed at 1 month after surgery. All the animals were gaining weight. The area of Elastin Patch looked smooth, with good motility, without obstruction. There were no leaks.

Thirteen animals were sacrificed between 2 and 4 months. The remaining 8 animals will be sacrificed between 4 and 5 months. All of the long term surviving animals are showing some degree of stenosis at the area of the healed duodenum, where the Elastin Patches were placed. The patch disappears within 7 weeks, with complete healing of the defect. The center of the defect shows coverage with mucosal cells, with hypertrophic changes around it. The future sacrifice at 4 months and 5 months will provide us with more information about how these findings are going to change. To better understand the mechanism of the healing process short term experiments were conducted, sacrificing 6 additional animals sequentially over 5 weeks. The repair technique designed for major duodenal injury, employed an Elastin/SIS Patch and bioabsorbable cyanoacrylate glue. Late stenosis formation at repair site is of major concern, and we should continue with our effort to improve this problem through better understanding of the healing process.

Studies in this segment: focused on (1) preparing several candidate absorbable cyanoacrylate based compositions (Compositions Nos. GF 70, GF 72, GF 74, GF 76, and GF 77) with improved adhesive strength retention for screening of the different candidate formulations by OMLC; (2) incorporating a safe dye into the cyanoacrylate based tissue adhesives (Compositions GF 71, GF 73, GF 75, GF 62D, GF 76D, GF 77D and GF 78D) without compromising their shelf lie and in vivo performance upon evaluation; (3) preparing, reproducibly, sufficient amounts of most promising tissue adhesives for evaluation at OMLC (Compositions Nos. GF 62, GF 62D and GF 72D); (4) preparation of a series of highly absorbable tissue adhesives with expected high compliance as cured films for evaluation in low load bearing applications at OMLC (Compositions Nos. HD 1, HD 2, HD 3 and HD 4); and (5) incorporating ground elastin and chopped PGA fibers in absorbable tissue adhesives for use as a hemostatic bandage (Compositions Nos. HB 1, HB 2 and HB 3).

Two new test methods, the nylon film and fabric cleavage test were developed and compared with the goat skin test method previously developed. Of the three methods, the fabric cleavage test was identified as the most reliable screening method. The experimental protocol was shared with the OMLC for use in their own screening studies.

Twenty-four domestic pigs were anesthetized and underwent celiotomy. A 2 cm circular defect was created at the second portion of the duodenum by scissors, excising half of its circumference. Our Elastin Patch, combined with SIS was applied to cover the defect using biodegradable cyanoacrylate glue and a few sutures then it was covered with omentum. Animals were followed by weight gain, endoscopic evaluation, and upper GI studies. After 2–5 months, animals were sacrificed to obtain specimens. One failed in 3 days due to a technical problem, and one failed in 20 days due to an abdominal abscess. All other 22 animals (22/24, 91.7%) did well, gaining weight. Early endoscopic studies (5–14d) showed an intact patch. Upper GI studies showed varying degree of stenosis at the repair site at 3–4 months. Sacrifice after 2–5 months showed complete healing of the defect, and dissolved patch. The subject Elastin Patch material provides a reliable barrier to repair duodenal injury and the biodegradable glue provides quick and easy water tight tissue fusion for our patch.

In an additional example, Elastin Patch was created from porcine aorta. After harvesting, it was preserved in 80% ethanol for 72 hours, then it was fully digested by soaking in 0.5M NaOH at 90 degrees centigrade with sonication. The digested aorta is cut into 4×4-cm patches. Two Elastin Patches were pressed together at 121 degrees centigrade for 15 minutes to form one bilaminar patch. The Elastin Patch was then packaged and sterilized at 121 degrees centigrade for 15 minutes.

SIS patch was made from fresh porcine swine intestinal segment. The tunica serosa and tunica muscularis were abraded by longitudinal wiping motion with a scalpel handle and moistened gauze. The remaining intestine is everted, and tunica mucosa was removed by the same manner of abrasion. The tube was then inverted to its original orientation. This was rinsed with saline several times and placed in 10% Neomycin sulfate solution and stored at 4 degrees centigrade. Decellularization was done by immersing the SIS in 2 mM SDS solution stirring with magnetic bar for 1.5 hours. This was then washed in the 0.01 MIPBS (pH 7.0) for 5 minutes, which was repeated 3–4 times. Finally, it was soaked in 0.01 M PBS (pH 7.0) with 10% Neomycin for storage.

Biodegradable cyanoacrylate glue was again provided by Poly-Med, Inc., Anderson, S.C. The glue composition was 95% Methoxypropyl Cyanoacrylate (MPC), and 5% L1 (Copolymer of lactide, glycolide, and caprolactone).

Figure 1A:
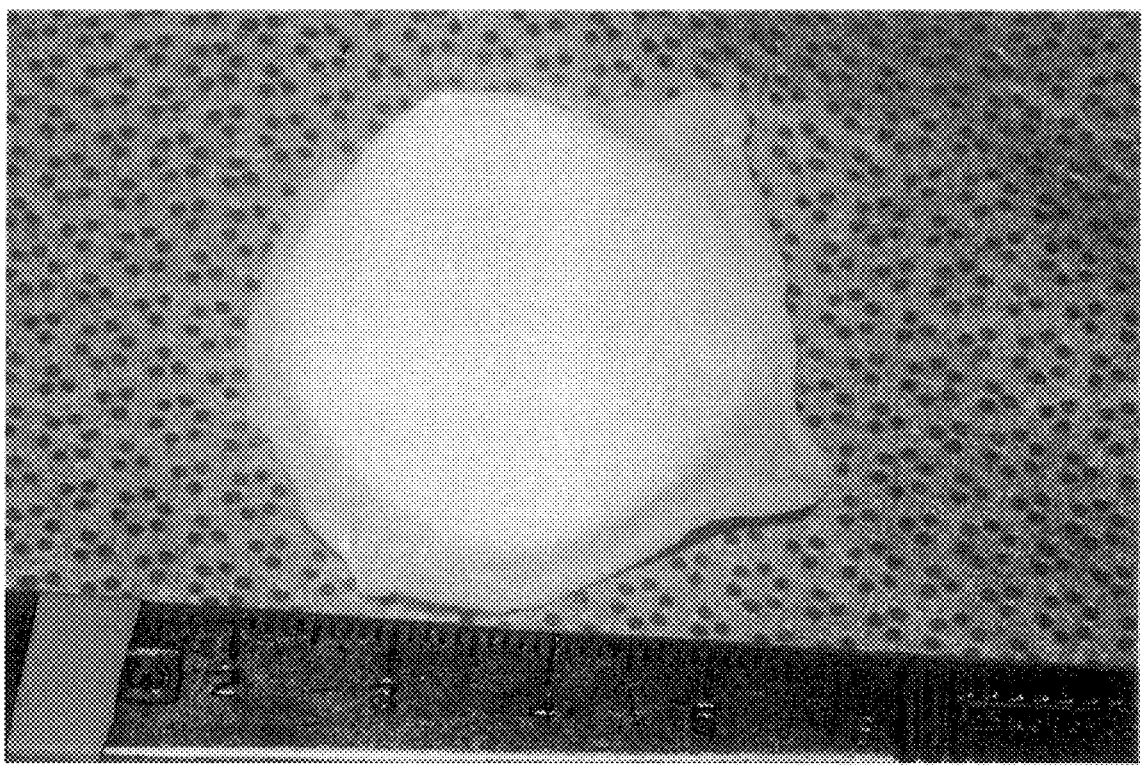
FIG. 1A is a photographical representation of a bilaminar Elastin/SIS composite patch of this invention.
Figure 2A:
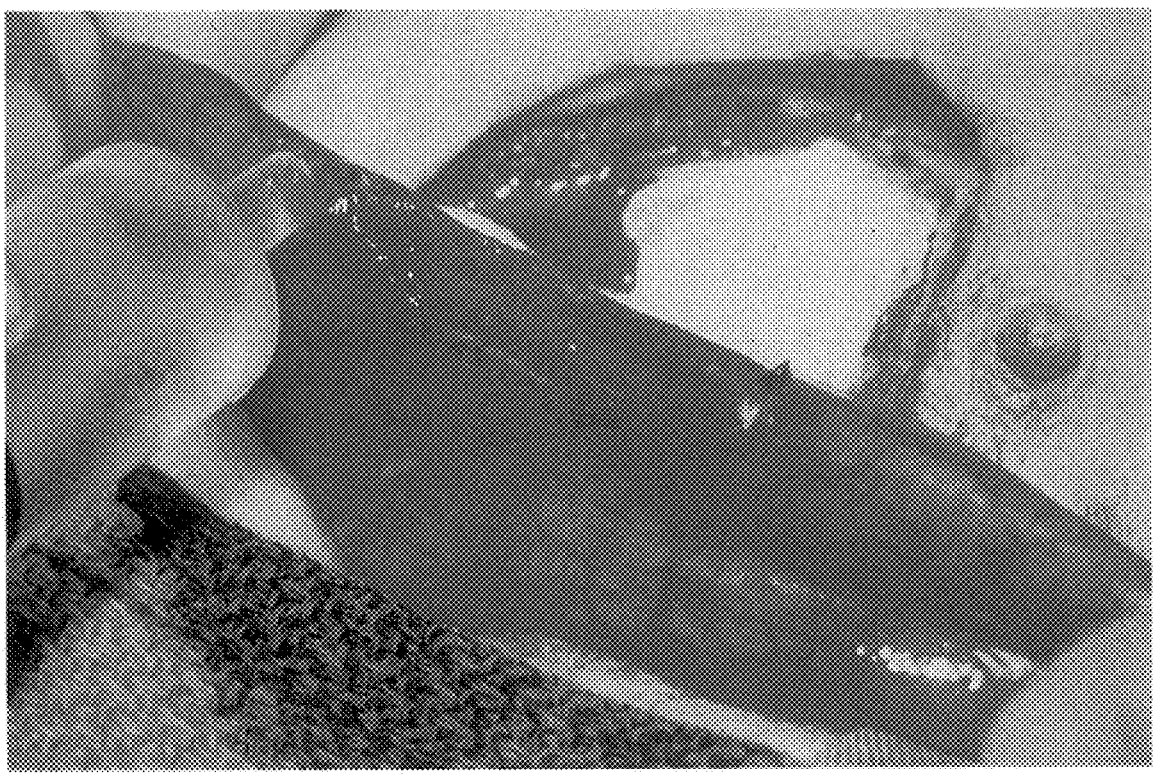
FIG. 2A is a phographical representation of the laminated Elastin Patch of FIG. 1A as applied to a duodenum employing a polycyanoacrylate glue (Poly-Med GF-62) as the adhesive medium.
Figure 3A:
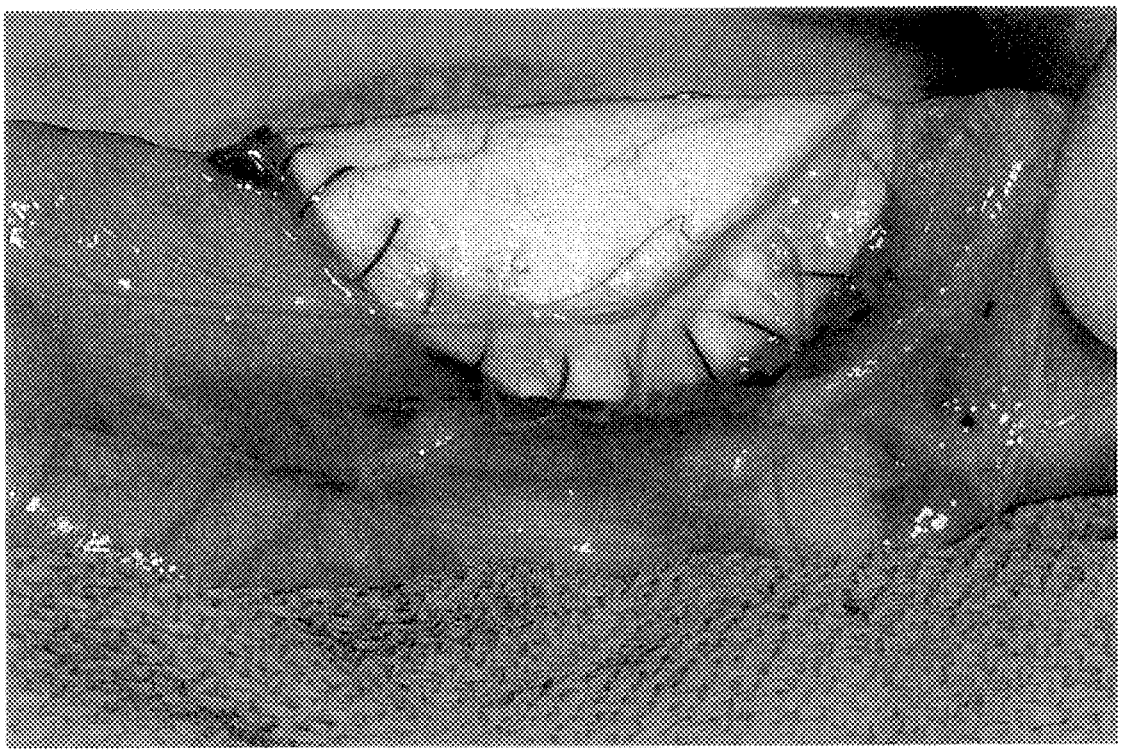
FIG. 3A is photographic representation of a completed duodenal repair in which a composite laminated patch is glued and sutured in place, without laceration, and then wrapped with omentum.

Twenty-four domestic pigs were anesthetized, and under sterile technique, underwent celiotomy. A circular defect of 2 cm in diameter was made on the second portion of the duodenum, excising half of its circumference. A circular Elastin Patch with a diameter of 3 cm was sandwiched between 4×4 cm of SIS sheet using biodegradable cyanoacrylate glue (See FIG. 1A. ). This composite Elastin Patch was adhered over the duodenal defect using the subject glue (See FIG. 2A), and a few interrupted sutures. This was covered by omentum and sutured to provide vascular supply to the area of repair (FIG. 3A).

Figure 5A:
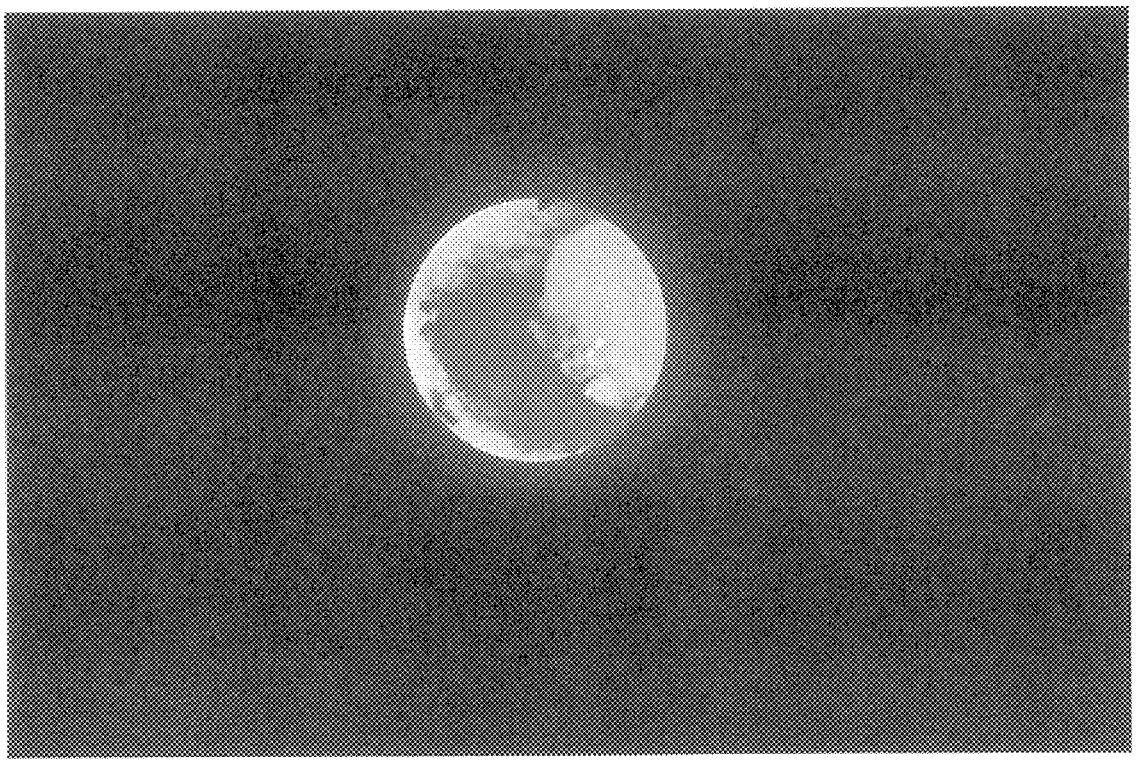
FIG. 5A is an endoscopic view of the laminated Elastin Patch 5 days after implantation.
Figure 6A:
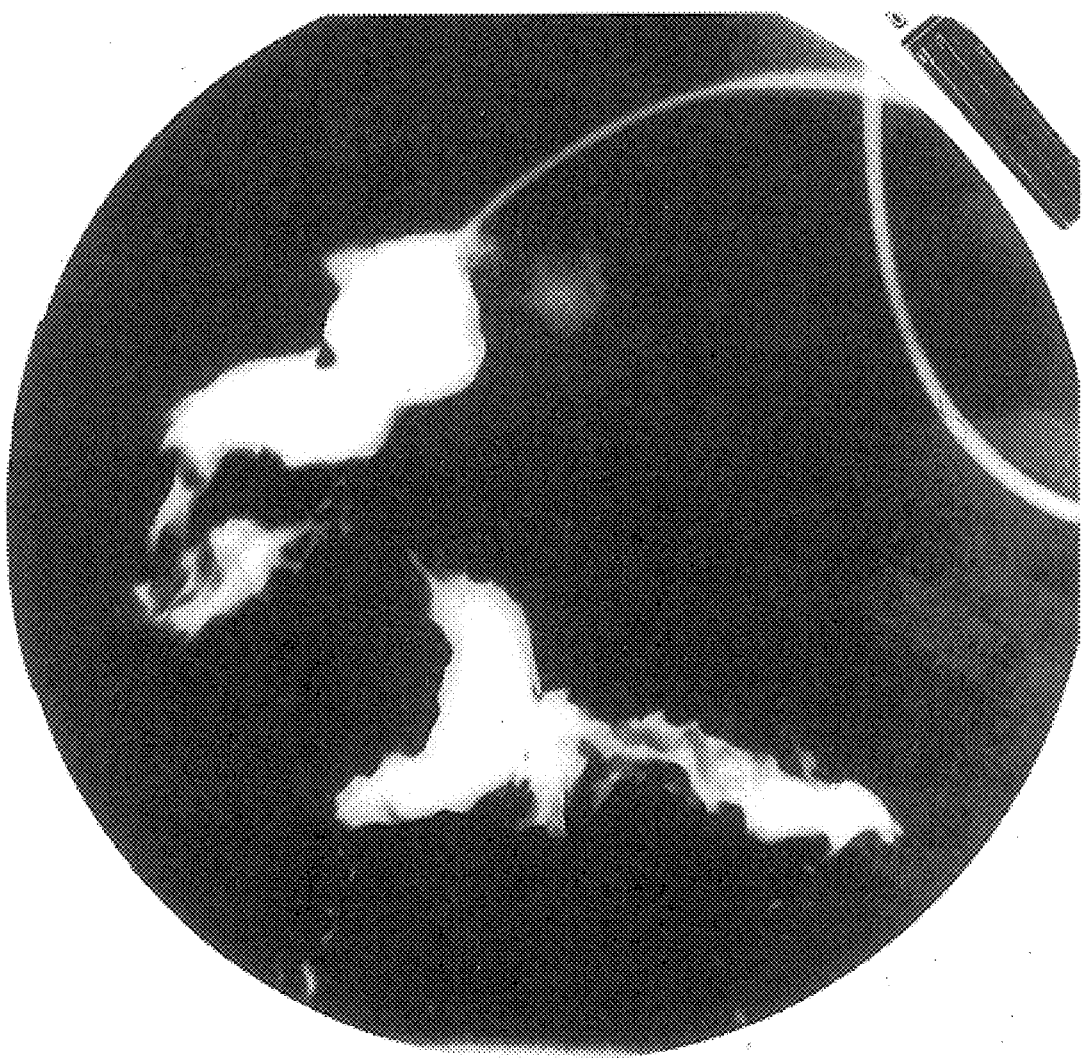
FIG. 6A is an upper GI contrast study, 2 weeks after implant of the laminated Elastin Patch.
Figure 7A:
FIG. 7A is a photographic representation of a gross specimen of the laminated Elastin Patch 3 months after implant.
Figure 8A:
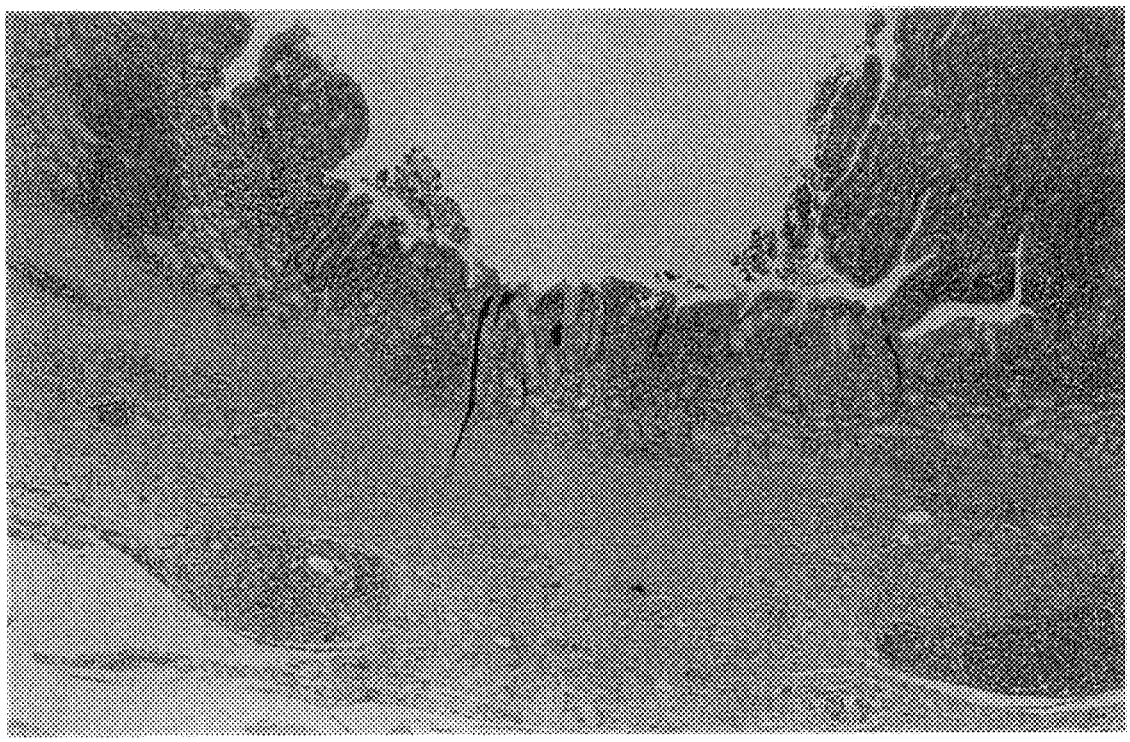
FIG. 8A depicts the histology of the laminated Elastin Patch.

Animals were allowed to resume regular feeding soon after surgery. No antibiotics or antacids were given after surgery. One animal had to be sacrificed at three days after surgery due to a technical problem. Another animal had to be sacrificed at three weeks after surgery due to an abscess confined to retroperitoneal space. The remaining twenty-two animals did very well, giving the success rate of 91.7% (22/24). They were able to resume oral feeding within the first hour after surgery. They were gaining weight following the normal growth curve of domestic pigs. One animal was sacrificed at seven weeks, one at two months, eleven at three months, seven at four months, and two at five months. Endoscopic study was performed at one and two weeks after surgery. The bilanior Elastin Patch was easily identified in the second portion of the duodenum, occupying up to half its circumference and there was no mechanical obstruction (FIG. 5A). Upper GI contrast studies showed flat stiffening, but no significant stricture or obstruction to the passage of contrast (FIG. 6A). Gross specimen of the sacrificed animals showed complete healing of the repair site with mucosal coverage as early as seven weeks, which appeared like a healed ulcer (FIG. 7A). Histology of the specimens after 7 weeks showed a completely healed duodenal wall with mucosal regeneration in the center (FIG. 8A). Submucosal tissue has also regenerated with incomplete regeneration of the muscular layer. Nerves were identified, but no ganglion ingrowth was seen. There was no remnant of the elastin or SIS identified in the specimen.

Unlike conventional repairs, the Elastin Patch duodenal patch of the present invention can be performed very easily, quickly, and reliably. The subject Elastin Patch was designed to provide reliable barrier for one to two weeks while tissue growth and regeneration into SIS takes place. The biodegradable cyanoacrylate provides an immediate water tight seal against the duodenal enzymes. Typically the surgical experiment was performed in thirty minutes from skin to skin. No other bowel resection or anastomosis is required, and the animals can resume oral feeding immediately after they recover from anesthesia. Healing occurs by both regeneration and contraction, leaving mild to moderate degree of stenoisis, but not as severe as one would expect from healing by contraction alone. The center of the healed scar showed evidence of muscosal regeneration. There was always a circular ridge of hypertrophied muscosa or submuscosal tissue around the center which is believed to be caused by the glue. In conclusion, the new Elastin Patch material provides a reliable barrier to repair major tissue defect in the second portion of the duodenum by combining this patch with SIS, a fairly strong material, resistant to infection and digestive enzymes can be obtained, while allowing the tissue to heal from outside. The modified cyanoacrylate glue provides quick and easy water tight tissue fusion for the Elastin Patch of the invention.

I claim:

1. A method for joining at least one layer of pressed biomaterial to a tissue substrate, comprising:
   providing the pressed biomaterial consisting essentially of elastin or tropoelastin materials;
   applying a biodegradable cyanoacrylate adhesive to either one of the material and the tissue; and
   adhering the pressed biomaterial to the tissue and forming a substantially water-tight engagement therebetween.

2. The method of claim 1, wherein pressing is conducted at a pressure of at least about 40 psi.

3. The method of claim 1, wherein pressing is conducted a temperature of at least about 50 degrees C.

4. The method of claim 1, wherein a suture can be effected without substantial tearing of the biomaterial.

5. The method of claim 1, wherein the cyanoacrylate adhesive comprises an alkoxy alkyl cyanoacrylate adhesive material.

6. The method of claim 1, wherein the tissue substrate comprises human tissue.

7. A method for producing a pressed biomaterial, comprising:
   providing at least one layer of an unpressed biomaterial consisting essentially of elastin or tropoelastin; and
   heating and pressing the unpressed biomaterial to form the pressed biomaterial which is capable of being attached to a tissue substrate for repair or replacement thereof.

8. The method of claim 7, wherein the pressed biomaterial comprises a multi-layer composite material.

9. The method of claim 7, wherein a suture can be effected without substantial tearing of the pressed biomaterial.

10. The method of claim 7, which further includes the step of adhering with an adhesive material the pressed biomaterial in water-tight engagement with the tissue substrate.

11. The method of claim 10, wherein the adhesive material comprises a cyanoacrylate material.

12. The method of claim 11, wherein the cyanoacrylate material comprises an alkoxy alkyl cyanoacrylate material.

13. The method of claim 7, wherein the tissue substrate comprises human or animal tissue.

14. The method of claim 7, wherein the pressed biomaterial is a bilaminar pressed biomaterial.

15. The method of claim 7, which further includes the step of suturing the pressed biomaterial to the tissue substrate.

16. The method of claim 7, wherein the pressing step is conducted in the presence of steam.

17. The product of claim 1, which comprises a pressed and steamed biomaterial.

18. The method of claim 7, wherein pressing is conducted at a pressure of at least about 40 psi.

19. The method of claim 7, wherein pressing is conducted at a temperature of at least about 50 degrees C.

20. A biomaterial product which comprises at least one layer of a pressed biomaterial consisting essentially of elastin or tropoelastin biomaterial which is capable of being attached to a tissue substrate for repair or replacement thereof.

21. The product of claim 20, wherein the pressed biomaterial comprises a multi-layer composite material.

22. The product of claim 20, which can receive a suture without substantial tearing of the pressed biomaterial.

23. The product of claim 20, which can be adhered with an adhesive material, the adhered biomaterial being in water-tight engagement with the tissue substrate.

24. The product of claim 23, wherein the adhesive material comprises a cyanoacrylate material.

25. The product of claim 24, wherein the cyanoacrylate material comprises an alkoxy alkyl cyanoacrylate material.

26. The product of claim 20, wherein the tissue substrate comprises human tissue.

27. The product of claim 20, wherein the pressed biomaterial is a bilaminar pressed biomaterial.

* * * * *

UNITED STATES PATENT AND TRADEMARK OFFICE
CERTIFICATE OF CORRECTION

PATENT NO. : 6,667,051 B1
DATED : December 23, 2003
INVENTOR(S) : Gregory

It is certified that error appears in the above-identified patent and that said Letters Patent is hereby corrected as shown below:

<u>Title page, item [54] and Column 1, line 3,</u>
Title, "AND OR" should read -- AND/OR --.

<u>Column 1,</u>
Line 43, "(Ooyambia et al," should read -- (Ooyama et al, --.
Line 46, "nonapeptide s have" should read -- nonapeptides have --.

<u>Column 4,</u>
Lines 17-18, "The file of this patent contains at least one drawing executed in color." should be deleted.

<u>Column 11,</u>
Line 13, "repair site. ¶Regarding" should read -- repair site. Regarding --.

<u>Column 18,</u>
Line 64, "segment: focused" should read -- segment focused --.

<u>Column 19,</u>
Line 60, "0.01 MIPBS" should read -- 0.01 M PBS --.

<u>Column 22,</u>
Line 11, "of claim 1, which" should read -- of claim 7, which --.

Signed and Sealed this

Twenty-second Day of March, 2005

JON W. DUDAS
*Director of the United States Patent and Trademark Office*